(12) United States Patent
Blesa et al.

(10) Patent No.: US 9,109,210 B2
(45) Date of Patent: Aug. 18, 2015

(54) ENHANCED PHYTASE VARIANTS

(75) Inventors: Stephane Blesa, Grisy-Suisnes (FR); Helene Chautard, Paris (FR); Marc Delcourt, Paris (FR); Laurent Mesta, Villefranche sur Saone (FR); Bruno Winter, Stuttgart (DE)

(73) Assignee: BIOMETHODES, Evry (FR)

( * ) Notice: Subject to any disclaimer, the term of this patent is extended or adjusted under 35 U.S.C. 154(b) by 701 days.

(21) Appl. No.: 13/380,694

(22) PCT Filed: Jul. 1, 2010

(86) PCT No.: PCT/EP2010/059413
§ 371 (c)(1),
(2), (4) Date: Dec. 12, 2012

(87) PCT Pub. No.: WO2011/000933
PCT Pub. Date: Jan. 6, 2011

(65) Prior Publication Data
US 2013/0122567 A1    May 16, 2013

(30) Foreign Application Priority Data
Jul. 1, 2009 (FR) ..................... 09 54490

(51) Int. Cl.
*C12N 9/16*    (2006.01)
(52) U.S. Cl.
CPC ........... *C12N 9/16* (2013.01); *C12Y 301/03008* (2013.01); *C12Y 301/03026* (2013.01)
(58) Field of Classification Search
CPC ...... C12N 9/16; A23K 1/1653; C07K 14/195; C12P 21/02; C12Y 301/03008; C12Y 301/03026
USPC .................... 435/196, 69.1; 424/63; 530/350
See application file for complete search history.

(56) References Cited

U.S. PATENT DOCUMENTS

2008/0263688 A1* 10/2008 Lassen et al. .................. 800/13

FOREIGN PATENT DOCUMENTS

WO    2007/128160 A1    11/2007

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Read et al., GenBank accession No. EEQ17187; Jun. 1, 2009.*
Fu et al.: "A highly pH-stable phytase from Yersinia kristeenseii: Cloning, expression, and characterization", Enzyme and Microbial Technology, vol. 42, No. 6, Feb. 2, 2008, pp. 499-505.
International Search Report of PCT/EP2010/059413; Jan. 1, 2011; Cupido Marinus.
Huoqing et al.: "A novel phytase from *Yersinia rohdei* with high phytase hydrolysis activity under low pH and strong pepsin conditions", Applied Microbiology and Biotechnology, vol. 80, No. 3, Jun. 12, 2008, pp. 417-426.
"Subname: Full=Phytase; EC=<A HREF="http://srs.ebi.ac.uk/srsbin/cgi-bin/wgetz?[enzyme-ECnumber:3.1.3.26]+-e>3.1.3.26</A>; retrieved from EBI accession No. UNIPROT:B4X9S4; Sep. 23, 2008.
"Subname: Full-Phytase"; retrieved from EBI accession No. UNIPROT: B6RGT1; Dec. 16, 2008.
"Subname: Full=Probable histidine acid phosphatase; Flags: Precursor"; retrieved from EBI accession No. UNIPROT: A1JTE2; Feb. 6, 2007.
Huang et al.:"A novel phytase with preferable characteristics from Yersinia intermedia", Biochemical and Biophysical Research Communications, vol. 350, No. 4, Dec. 1, 2006, pp. 884-889.

* cited by examiner

*Primary Examiner* — Delia Ramirez
(74) *Attorney, Agent, or Firm* — Amster, Rothstein & Ebenstein LLP

(57) ABSTRACT

The present invention provides the field of enhancing proteins and in particular to that of proteins enhanced by molecular change. It provides a variant of a phytase that is termed enhanced in that is has better thermostability and/or activity than the original phytase. The invention also provides a nucleic acid coding for said variant, a cassette or an expression vector containing said variant, a host cell expressing said variant, a composition comprising said variant and uses thereof, principally in the preparation of food additives and animal feed.

18 Claims, 5 Drawing Sheets

ENHANCED PHYTASE VARIANTS

BACKGROUND OF THE INVENTION

The present invention relates to the field of enhancing proteins, in particular that of proteins enhanced by molecular change. It pertains to a variant of a phytase, termed enhanced, in that it has better thermostability and/or activity compared with the original phytase. The invention also pertains to a nucleic acid coding for said variant, to a cassette or an expression vector containing said variant, to a host cell expressing said variant, to a composition comprising said variant, and also to the uses thereof, principally in the preparation of food additives and animal feed.

Phytate is the principal phosphorus storage compound in plants. This molecule, also known as phytic acid or inositol-hexa-phosphate (InsP6 or myo-inositol hexakisphosphate), consists of a cyclohexane to which six phosphate groups are bonded. The phytate represents approximately 70% of plant phosphate, the remaining 30% being present in the free form. Further, phosphate residues of phytate chelate divalent and trivalent cations such as calcium, iron, zinc, magnesium, copper, manganese and molybdenum, which are essential for nutrition.

Figure 1:
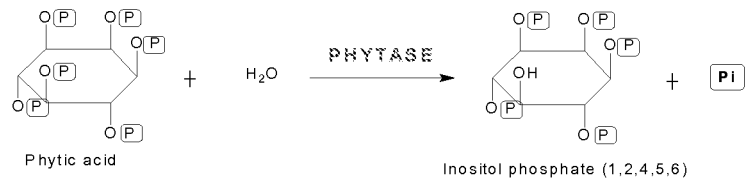

Phytases are enzymes that hydrolyze phytate: such enzymes naturally release one or two phosphates, rarely three, which can then be adsorbed into the digestive system; other reaction products are rarely inositol-tri-phosphate, principally inositol tetra- and penta-phosphate (FIG. 1). Phytases constitute a family of enzymes that is widely represented in nature: many organisms, from the bacterium to the plant via fungi and certain animals, express one or more of them. However, mammals do not express any; ruminants or polygastric animals such as cattle and horses have endogenous microorganisms in their gastrointestinal tract that can degrade the phytate, but this does not apply with monogastric animals, principally pigs and poultry, for example, and so the phytate originating from ingested plants does not represent a useful source of phosphorus. Thus, it is necessary to add free phosphates to their feed. However, a portion of those added free phosphates and practically all of the phytate ingested by the animals are discharged into the environment. The phytate is then degraded by bacteria in the ground and ends up in the ground water and rivers in the form of free phosphate. In regions with a high concentration of stock farming, such agro-industrial phosphate waste, in the free form or in the form of phytate, represents a major source of pollution, which in particular results in the proliferation of green algae in rivers and watercourses. In addition to the esthetic aspect, such algae have a major ecological impact since they compete with local plant species, in particular as regards consumption of dissolved oxygen.

One way of being able to use phosphate stored in the form of phytate as a source of phosphate by mammals is to introduce exogenous phytase into food. Adding said enzyme thus represents an alternative to using inorganic phosphate as a food supplement. Further, by rendering the phosphate of the phytate accessible, they can also provide better accessibility to metallic ions chelated onto the phosphate of the phytate, as well as to proteins bonded to the phytate, rendering them nutritionally available. Phytases are currently used relatively systematically in animal feed. They are used as a partial replacement for phosphates and they also render proteins, amino acids, and calcium more accessible.

However, there are several limitations to using phytases in animal feed:

the insufficient effectiveness of phytases in releasing phosphates constitutes a first limitation. Phosphates are still added to animal feed, even in the presence of exogenous phytases. However, if all of the phytate were to be converted into free phosphates, supplements would no longer be required; thus, there is a genuine need to propose more active phytases;

the majority of enzymes in current use cannot be added directly to feed, since they cannot withstand the granulation process, which involves heating the feed to 95° C. for 90 seconds. The enzymes are thus sprayed onto the feed after the granulation stage, which represents an additional cost and constitutes a second limitation; thus, there is great demand for the availability of more thermostable phytases.

The aim of the present invention is to overcome current limitations by generating a phytase that is sufficiently active to have a substantial impact on the need for supplementing with phosphates and is sufficiently thermostable to be able to be added directly to the feed of animals, without having to use a spraying technique.

Many phytases have featured in publications and patent applications, or are even already in use in agro-industrial applications. However, none of them have been able to dispense with the need for supplementing stock farm animal feed with phosphates, and none of them is sufficiently thermostable to be added directly to animal feed without having to use a spraying technique.

The majority of publications pertain to phytases from *Aspergillus niger* and *Escherichia coli*. Other phytases of microbial origin or deriving from plants have also been studied, the problem being to obtain thermostable phytases having a specific activity that is greater than that of *Aspergillus niger* (250 U/mg). The phytases described in the literature and the patent applications deal with fungi (basidiomycetes and ascomycetes), yeasts and bacteria.

Many phytases have been isolated from fungi and derive in the main from the *Aspergillus* family, but from *Absidia, Acrophiaiophora, Agrocybe, Calcarisporiella, Cheatomium, Corynascus, Mucor, Mycelia, Myriococcurn, Penicillium, Peniophora, Rhizomucor, Rhizopus* or even from *Trametes, Sporotrichum, Neurospora, Trichoderma, Cladosporium, Myceiiophthora, Taleromyces, Thielavia, Humicola, Paxillus* and *Thermoascus*.

A great deal of information is available regarding the specific activities and Km of such enzymes, such as that in Wyss et al 1999 (Appl. Environ. Microbiol. 65 (2) 367-373). Overall, *Aspergillus* phytases are characterized by high Km values of 5 µM to 20 µM, an optimum temperature of 57° C. and an optimum pH of 5.5 except for *Aspergillus fumigatus* (opt pH.=6), but have very low specific activities ranging from 100 to 250 U/mg.

Certain phytases deriving from other fungi have exhibited interesting properties, in particular high specific activities, such as the phytase from *Trametes pubescens* or the phytase from *Peniophora lycii* (respectively 1200 U/mg and 1080 U/mg in WO 98/28408). *Cladosporium* sp. has an interesting phytase with a specific activity of 900 U/mg and a Km of 15.2 µM, but has a low optimum temperature of 40° C. In addition, the 6-phytase from *Ceriporia* sp. has a specific activity of 11040 U/mg. Some complementary information was published by Lassen et al, 2001 (Appl. Environ. Microbiol. 67 (10) 4701-4707, comparing the thermostability of phytases from basidiomycetes, in particular *Peniophora lycii, Ceriporia* sp., *Trametes pubescens* and *Aspergillus niger*; it appears that said enzymes have Tms (temperature at which the enzyme is 50% active) that are quite close, from 55° C. (*Trametes pubescens*) to 60° C. (*Peniophora lycii*) but have residual activities (percentage activity resulting from preincubation for 60 minutes at 80° C. in sodium acetate [0.1 M], pH 5.5) that vary widely, from 15% (*Trametes pubescens*) to 62% (*Peniophora Lycii*).

Many establishments have filed patent applications concerning said enzymes, in particular Danisco/Genencor (WO 2001/012792, *Penicillium subtilis*; WO 2003/038035, *Trichoderma reesei*; WO 2003/038111, *Penicillium, Mumicola, Emericella, Fusarium*), ABEnzymes/ROAL (EP 0 659 215, *Aspergillus* phytases produced by *Trichoderma reesei*), DSM/Roche (EP 0 684 313, *Apergillus terreus, Aspergillus fumigatus, Aspergillus nidulans, Talaromaces thermophilus*), BASF (WO 2003/102174, *Aspergillus*), Adisseo (WO 2003/054199, *Penicillium*), and Choongang Biotech Ltd. (WO 2005/056835, *Penicillium oxalicum*).

Several bacterial phytases have been described that originate from *Bacillus subtilis* (Paver and Jagannathan, 1982, Journal of Bacteriology 151:1102-1108), *Pseudomonas* (Cosgrove, 1970, Australian Journal of Biological Sciences 23:1207-1220), and *Klebsiella*. Several phytases originating from *E. coli* have been reported in the literature. Greiner et al, in Arch, Biochem. Biophys., 303, 107-113, 1993, purified and characterized a novel phytase of *E. coli*; others have been reported by Lim et al., 2000, Nat. Struct. Biol. 7: 108-113, Oshima et al., 1996, DNA Research, 3:137-155, Touati and Danchin, 1987, Biochimie, 69:215-221, Rodriguez et al., 2000, Arch. Biochem. Biophys., 382:105-112, Kretz, U.S. Pat. No. 5,876,997 from *E. coli* B, and appA by Dassa et al., 1990, J. Bacteriol. 172:5497-5500.

Mutants from *E. coli* phytase have been obtained by genetic engineering, resulting in enhanced thermostabilities and specific activities (Rodriguez et al, 2000, Arch. Biochem. Biophys., 382:105-112, Lanahan et al., 2003, US patent application 20030157646). However, none of those mutations could be used to produce sufficient of those enzymes of prokaryotic origin in eukaryotic production organisms.

The aim of the present invention is to provide a recombinant enzyme that is suitable for industrial processes to allow it to be used as a food additive, principally in animal feed.

In the application WO 2002/048332, using a BLAST analysis of bacterial genomes available at the date of the invention and using the appA gene from *E. coli*, Diversa identified a novel protein from *Yersinia pestis* having phytase activity. That protein had a remarkable feature, namely that it has a specific activity of 4400 U/mg. No other biochemical features of that protein were specified in that application. That application appears to demonstrate a high potential activity for phytase originating from bacteria from the *Yersinia* family.

On Oct. 20, 2005, the protein sequence with reference ZP_00832361 was added to the NCBI database. Said sequence is that of a hypothetical protein of *Yersinia intermedia* ATCC 29909 the corresponding nucleotide sequence for which is presented under reference numeral NZ_AALF01000052, region: 1889 . . . 3214. That protein sequence was obtained by translation of the corresponding nucleotide sequence originating from the complete sequence for the genome of the strain *Yersinia intermedia* ATCC 29909. Although the PRK10172 domain appears to predict a phytase activity, no experimental element accompanied that prediction.

This appears to have been confirmed by the isolation of a very similar phytase from a novel strain of *Yersinia intermedia* originating from a dirt sample from a glacier, denoted H-27 and presented in the application WO 2007/128160. The phytase derived from the H-27 strain is designated in the NCBI database with accession number AB195370.1 for the nucleotide sequence and DQ986462 for the protein sequence; it has 98% identity as regards the amino acids and 97% identity with the nucleotide sequence encoding the hypothetical phytase of *Yersinia intermedia* ATCC 29909.

The phytase of application WO 2007/128160 has a high specific activity of more than 3000 U/mg, of the same order as the specific activity recorded for *Yersinia pestis* in WO 2002/048332. In that application WO 2007/128160, the intrinsic biochemical characteristics of the protein are claimed, namely a molecular weight of 45.5 kDa, an optimum pH in the range 4.0 to 5.0, an optimum temperature in the range 50 to 60° C., a theoretical pI of 7.7, a specific activity of more than 3000 U/mg and a high resistance to pepsin and trypsin.

BRIEF SUMMARY OF THE INVENTION

The present invention means that current limits can be exceeded, by proposing an enhanced variant by changing the phytase from *Yersinia intermedia* molecularly. The term "enhanced variant" means a variant with a thermostability and/or activity higher than the original phytase from *Yersinia intermedia*, meaning that it can be used in industrial processes and in particular as a food additive.

As is described in the remainder of the text and with the aid of the accompanying figures, the present application describes an enhanced variant of a phytase whose sequence is SEQ ID No. 1 or a functional derivative thereof, characterized in that it comprises at least one substitution on one of the amino acids from the group consisting of P3, V4, A5, P8, T9, G10, V16, V17, L19, S20, R21, H22, G23, V24, R25, S26, P27, T28, K29, Q30, T31, Q32, L33, M34, D36, P39, K41, W45, A49, G50, Y51, L52, T53, G56, A57, V60, Y67, G75, A78, C81, D92, V93, D94, Q95, R96, T97, R98, L99, T100, G101, A103, V116, V125, D126, F129, H130, P131, V132, D133, D140, T142, Q143+H145, A147, L152, P155, L156, E158, E158+S160, F167, A177, C182, G189, D193, N196, F197, K201, K206, P207, T209, K210, V211, S212, L213, L217, A218, L219, S220, S221, T222, L223, G224, E225, I226, F227, L228, L229, Q230, N231, Q233, A234, P236, R242, I250, S251, L252, L253, L255, H256, N257, Q259, F260, D261, M263, A264, Y268, K273, G274, P276, L277, Q292, G293, P297, P300, Q301, G308, G309, H310, D311, T312, N313, I314, A315, N316, G322, A323, Q326, P331, D332, N333, T334, P335, P336, G337, G338, G339, V341, E343, D349, Q352, R353, Y354, I355, A370, E371, K376, P379, A380, G381, D388, E391, S393, G394 and P414, the positions being indicated in SEQ ID No.1. Preferably, the enhanced phytase variant whose sequence is SEQ ID No.1 or a functional derivative thereof comprises at least one substitution selected from the group consisting of P3L, P3V, V4G, A5P, P8N, P8V, T9I, T9Q, T9S, T9Y, G10A, G10P, V16M, V17W, L19G, S20C, R21F, H22A, H22S, H22Y, G235, V24C, R25C, S26C, P27F, T28N, T28S, T28V, K29N, Q30C, Q30D, Q30R, Q32R, L33R, M34C, D36N, P39N, K41G, W45C, G50D, G50E, Y51G, Y51N, Y51Q, Y51W, L52C, L52G, T53C, G56C, A57C, V60I, Y67F, Y67W, G75R, A78P, C81N, D92R, V93G, D94G, D94S, Q95N, Q95V, R96A, T97N, R98N, R98T, L99C, G101C, A103C, V116C, V125N, D126Q, F129W, H130N, H130Q, H130R, H130W, H130Y, P131S, V132W, D133G, D133P, D133R, D133V, D133W, D140E, D140F, D140N, T142N, Q143N+H145T, A147C, L152N, L152P, P155N, P155T, L156N, E158N, E158N+S160T, F167N, A177N, A177S, A177T, C182N, G189N, D193C, N196C, F197V, K201N, K206A, P207N, P207S, P207T, T209C, K210C, K210E, K210N, K210S, K210T, K210V, K210Y, V211C, V211G, S212N, L217N, A218N, L219V, S220N, L223S, E225D, F227S, L229H, Q230N, Q230T, N231K, Q233S, Q233T, A234K, P236N, R242N, I250S, I250T, S251N, L252M, L255T, H256A, H256E, H256P, N257I, Q259K, Q259S, Q259T, Q259Y, D261F, M263L, A264N, A264P, Y268C, Y268E, Y268N, K273N, G274C, G274S, P276L, Q292P, G293N, P297N, P297S, P300N, Q301L, G308S, H310N, H310R, D311A, D311E, D311G, T312D, T312N, T312P, T312V, N313F, N313R, I314E, I314M, N316C, G322C, A323E, Q326S, Q326T, P331R, D332A, D332L, D332N, D332Q, N333V, P335C, P335G, P335R, P335S, P335T, G339C, V341A, V341E, E343A, E343G, D349N, D349S, D349T, Q352S, Q352T, R353C, Y354N, I355W, A370D, A370T, E371S, E371T, K376S, P379L, P379S, P379T, A380S, A380T, G381S, D388C, E391N, S393G, G394S, G394T and P414Q, the positions being indicated in SEQ ID No.1. Preferably, the enhanced phytase variant whose sequence is SEQ ID No.1 or a functional derivative thereof comprises at least one combination of substitutions selected from the substitutions of the preceding group.

SEQ ID No.1 is the sequence appearing in the NCBI database filed on Oct. 20, 2005 with accession number ZP_00832361, but not, however, containing the 23 amino acid signal sequence at the 5 end of the protein. SEQ ID No.1 thus corresponds to residues 24-441 appearing under the above-mentioned accession number. SEQ ID No.1 also contains the nucleic acid sequence coding for the preceding protein sequence in the NCBI base with reference NZ_AALF01000052. A nucleic acid coding for a variant of the present invention can readily be prepared on the basis of this sequence using techniques that are well known to the skilled person, for example by directed mutagenesis of the codon to be modified, to obtain the desired amino acid substitution. Thus, the sequence for the enhanced phytase variant of the present invention corresponds to SEQ ID No.1 including the selected substitution or substitutions.

SEQ ID No.2 reproduces only the protein sequence of SEQ ID No.1.

In a particular embodiment, the enhanced variant of the present invention comprises a single substitution.

In a preferred embodiment, the enhanced variant of the present invention or a functional derivative thereof comprises at least one substitution on one of the amino acids from the group consisting of K29, Q30, Y51, L52, G75, C81, V93, Q95, R98, L99, F129, H130, D140, T142, P155, F167, A177, G189, K201, K210, L219, I250, S251, L252, L255, M263, Y268, G274, Q292, G293, P297, G308, N316, Q326, D349 and E391, the positions being indicated in SEQ ID No.1. In another preferred embodiment, the enhanced variant of the present invention or a functional derivative thereof comprises substitutions on one of the amino acids from the group consisting of K29, Q30, Y51, L52, G75, G81, V93, Q95, R98, L99, F129, H130, D140, T142, P155, F167, A177, G189, K201, K210, L219, I250, S251, L252, L255, M263, Y268, G274, Q292, G293, P297, G308, N316, Q326, D349 and E391, the positions being indicated in SEQ ID No.1. Preferably, the substitutions on the amino acids K29, Q30, Y51, L52, G75, C81, V93, Q95, R98, L99, F129, H130, D140, T142, P155, F167, A177, G189, K201, K210, L219, I250, S251, L252, L255, M263, Y268, G274, Q292, G293, P297, G308, N316, Q326, D349 and E391, are selected from the group consisting of K29N, Q30D, Y51G, Y51N, Y51Q, Y51W, L52G, G75R, C81N, V93G, Q95N, R98T, L99C, F129W, H130Y, D140F, D140N, T142N, P155N, P155T, F167N, A177N, A177S, A177T, G189N, K201N, K210N, K210S, L219V, I250S, I250T, S251N, L252M, L255T, M263L, Y268N, G274C, Q292P, G293N, P297N, G308S, N316C, Q326S, Q326T, D349S, D349T and E391N, the positions being indicated in SEQ ID No.1.

In a yet more preferred embodiment, the enhanced variant of the present invention or a functional derivative thereof comprises substitutions on one of the amino acids from the group consisting of K29, Q30, Y51, L52, G75, V93, R98, L99, F129, H130, D140, T142, P155, F167, A177, K201, K210, L219, 5251, L252, L255, M263, Y268, G274, Q292, G293, G308, N316, Q326 and E391, the positions being indicated in SEQ ID No.1. Preferably, the substitutions on the above amino acids are selected from the group consisting of K29N, Q30D, Y51G, Y51Q, Y51W, L52G, G75R, V93G, R98T, L99C, F129W, H130Y, D140F, T142N, P155T, F167N, A177N, A177S, A177T, K201N, K210S, L219V, S251N, L252M, L255T, M263L, Y268N, G274C, Q292P, G293N, G308S, N316C, Q326S, Q326T and E391N, the positions being indicated in SEQ ID No.1.

In another particular embodiment, the enhanced variant of the present invention or a functional derivative thereof comprises a combination of substitutions selected from the group consisting of G274C+N316C, T142N+A177T+Q326T, K210S+Y268E+Q292P, D140F+Y268E+Q292P, F167N+Y268E+Q292P, T142N+A177T+K210S+Q326T, T142N+A177T+K210S+Y268E+Q292P+Q326T, T142N+A177T+K210S+Y268E+Q292P+Q326T+G274C+N316C, L52C+L99C+T142N+A177T+K210S+Y268E+Q292P+Q326T, the positions being indicated in SEQ ID No.1. In a preferred mode of this particular embodiment, the enhanced variant of the present invention or a functional derivative thereof comprises a combination of substitutions consisting of T142N+A177T+K210S+Y268E+Q292P+Q326T, the positions being indicated in SEQ ID No.1. In another particularly preferred mode of this embodiment, the enhanced variant of the present invention or a functional derivative thereof comprises a combination of substitutions consisting of T142N+A177T+K210S+Y268E+G274C+Q292P+N316C+Q326T, the positions being indicated in SEQ ID No.1. In another preferred mode of this particular embodiment, the enhanced variant of the present invention or a functional derivative thereof comprises a combination of substitutions consisting of T142N+A177T+K210S+Q326T, the positions being indicated in SEQ ID No.1. In another preferred mode of this particular embodiment, the enhanced variant of the present invention or a functional derivative thereof comprises a combination of substitutions consisting of G274C+N316C, the positions being indicated in SEQ ID No.1. In another preferred mode of this particular embodiment, the enhanced variant of the present invention or a functional derivative thereof comprises a combination of substitutions consisting of T142N+A177T+Q326T, the positions being indicated in SEQ ID No.1. In another preferred mode of this particular embodiment, the enhanced variant of the present invention or a functional derivative thereof comprises a combination of substitutions consisting of K210S+Y268E+Q292P, the positions being indicated in SEQ ID No.1. In another preferred mode of this particular embodiment, the enhanced variant of the present invention or a functional derivative thereof comprises a combination of substitutions consisting of D140F+Y268E+Q292P. In another preferred mode of this particular embodiment, the enhanced variant of the present invention or a functional derivative thereof comprises a combination of substitutions consisting of F167N+Y268E+Q292P.

The present invention provides an enhanced variant of a phytase whose sequence is SEQ ID No.1 or a functional derivative thereof comprising the selected substitution or substitutions.

The present invention also provides a nucleic acid coding for an enhanced phytase variant in accordance with the present invention or a functional derivative thereof, an expression cassette comprising a nucleic acid of the present invention, and a vector comprising a nucleic acid or an expression cassette of the present invention. The vector may preferably be selected from a plasmid, a phage, a phagemid and a viral vector.

The present invention also provides a composition comprising at least one enhanced phytase variant the sequence for which is SEQ ID No.1 or a functional derivative thereof with the selected substitution or substitutions in accordance with the present invention. It also provides any solid, liquid or gaseous mixture comprising a certain percentage of at least one enhanced phytase variant of the present invention. It also provides mixtures preferably containing one, two, three, four, five or ten enhanced phytase variants in accordance with the present invention or functional derivatives thereof. The present invention also provides phytase preparations or compositions containing a certain percentage of at least one enhanced phytase variant of the present invention or a functional derivative thereof and one or more other enzymes having advantageous properties.

The present invention provides the use of an enhanced phytase variant of the invention or a functional derivative thereof, for the preparation of a food additive. Using an enhanced phytase variant of the present invention or a functional derivative thereof is of concern to industrial processes that can be used to liberate minerals and in particular phosphate from plants, either in vitro when treating food before ingestion using the enhanced phytase variant of the present invention, or in vivo by administering said variant directly to animals before or with their feed.

The present invention provides the use of a nucleic acid, an expression cassette or a coding vector and/or containing at least one enhanced phytase variant whose sequence is SEQ ID No.1 or a functional derivative thereof with the selected substitution or substitutions of the present invention, to transform or transfect a host cell. It also provides a host cell comprising a nucleic acid, an expression cassette or a vector coding for an enhanced phytase variant of the present invention or a functional derivative thereof. The present invention also provides the use of said nucleic acid, said expression cassette, said vector or said host cell to produce an enhanced phytase variant of the present invention or a functional derivative thereof. It also provides a method of the production of an enhanced phytase variant of the present invention, comprising transforming or transfecting a host cell with a nucleic acid, an expression cassette or a vector of the present invention, culturing the transformed or transfected host cell and harvesting the enhanced phytase variant or a functional derivative thereof produced by the host cell. The host cell may be prokaryotic or eukaryotic. Thus, the host cell may be a microorganism, preferably a bacterium, a yeast or a fungus. The host cell may also be a mammalian cell such as a COS7 or CHO cell.

The term "functional derivative" means any enzyme derived from the phytase variant of the present invention comprising structural modifications while retaining phytase activity. Such modifications may, for example, involve extending the enzyme by adding new domains, or partial or complete substitutions of domains such as replacing stretches of amino acids by amino acids from other enzymes that might provide other functions/properties. The term "functional derivative" also includes a dimerized form of the variant of the enzyme of the present invention, which may be homo- or heterodimeric, or even polymeric, having enhanced properties such as thermostability, for example, because of domain multiplication. The term "functional derivative" also encompasses a chimeric form of the phytase variant of the present invention, fused with another protein/enzyme of interest or with one or more domains of said enzyme of interest. The term "functional derivative" also encompasses a functional fragment of the phytase variant of the present invention that preserves phytase activity. Said activity may be measured using one of the protocols described in Examples 4 and 5. The fragment may comprise 250, 275, 300, 325, 350, 375, 380, 385, 390, 395, 400, 405, 410 or 415 consecutive amino acids of the phytase of the present invention. Said functional fragment may also be dimerized or polymerized and/or fused with another protein/enzyme of interest or with one or more domains thereof.

The term "variant" or "mutant" means a nucleotide sequence having mutations compared with a reference nucleotide sequence. Said mutations may be silent due to degeneracy of the genetic code; the protein encoded by the variant is then identical to the protein encoded by the reference nucleotide sequence. Said mutations may also cause substitutions of amino acids in the protein encoded by the variant compared with the protein encoded by the reference nucleotide sequence. The term "variant" includes sequences containing mutations obtained by directed mutagenesis. The expression "variant" is attributed to nucleotide sequences as well as to protein sequences encoded by said nucleotide sequences, presenting said mutations.

The enhanced phytase variant of the present invention or a functional derivative thereof may comprise substitutions on one of the amino acids from the group consisting of P3, V4, A5, P8, T9, G10, V16, V17, L19, S20, R21, H22, G23, V24, R25, S26, P27, T28, K29, Q30, T31, Q32, L33, M34, D36, P39, K41, W45, A49, G50, Y51, L52, T53, G56, A57, V60, Y67, G75, A78, C81, D92, V93, D94, Q95, R96, T97, R98, L99, T100, G101, A103, V116, V125, D126, F129, H130, P131, V132, D133, D140, T142, Q143+H145, A147, L152, P155, L156, E158, E158+S160, F167, A177, C182, G189, D193, N196, F197, K201, K206, P207, T209, K210, V211, S212, L213, L217, A218, L219, S220, S221, T222, L223, G224, E225, I226, F227, L228, L229, Q230, N231, Q233, A234, P236, R242, I250, S251, L252, L253, L255, H256, N257, Q259, F260, D261, M263, A264, Y268, K273, G274, P276, L277, Q292, G293, P297, P300, Q301, G308, G309, H310, D311, T312, N313, I314, A315, N316, G322, A323, Q326, P331, D332, N333, T334, P335, P336, G337, G338, G339, V341, E343, D349, Q352, R353, Y354, I355, A370, E371, K376, P379, A380, G381, D388, E391, S393, G394 and P414 not described in the group P3L, P3V, V4G, A5P, P8N, P8V, T9I, T9Q, T9S, T9Y, G10A, G10P, V16M, V17W, L19G, S20C, R21F, H22A, H22S, H22Y, G23S, V24C, R25C, S26C, P27F, T28N, T28S, T28V, K29N, Q30C, Q30D, Q30R, Q32R, L33R, M34C, D36N, P39N, K41G, W45C, G50D, G50E, Y51G, Y51N, Y51Q, Y51W, L52C, L52G, T53C, G56C, A57C, V60I, Y67F, Y67W, G75R, A78P, C81N, D92R, V93G, D94G, D94S, Q95N, Q95V, R96A, T97N, R98N, R98T, L99C, G101C, A103C, V116C, V125N, D126Q, F129W, H130N, H130Q, H130R, H130W, H130Y, P131S, V132W, D133G, D133P, D133R, D133V, D133W, D140E, D140E, D140N, T142N, Q143N+H145T, A147C, L152N, L152P, P155N, P155T, L156N, E158N, E158N+ S160T, F167N, A177N, A177S, A177T, C182N, G189N, D193C, N196C, F197V, K201N, K206A, P207N, P207S, P207T, T209C, K210C, K210E, K210N, K210S, K210T, K210V, K210Y, V211C, V211G, S212N, L217N, A218N, L219V, S220N, L223S, E225D, F227S, L229H, Q230N, Q230T, N231K, Q233S, Q233T, A234K, P236N, R242N, I250S, I250T, S251N, L252M, L255T, H256A, H256E, H256P, N257I, Q259K, Q259S, Q259T, Q259Y, D261F, M263L, A264N, A264P, Y268C, Y268E, Y268N, K273N, G274C, G274S, P276L, Q292P, G293N, P297N, P297S, P300N, Q301L, G308S, H310N, H310R, D311A, D311E, D311G, T312D, T312N, T312P, T312V, N313F, N313R, I314E, I314M, N316C, G322C, A323E, Q326S, Q326T, P331R, D332A, D332L, D332N, D332Q, N333V, P335C, P335G, P335R, P335S, P335T, G339C, V341A, V341E, E343A, E343G, D349N, D349S, D349T, Q352S, Q352T, R353C, Y354N, I355W, A370D, A370T, E371S, E371T, K376S, P379L, P379S, P379T, A380S, A380T, G381S, D388C, E391N, S393G, G394S, G394T and P414Q, the positions being indicated in SEQ ID No.1, or combinations of substitutions derived from said group, as mentioned above. As an example, said substitutions may be substitutions termed "conservative", i.e. substitutions within a group of amino acids having similar or equivalent characteristics, such as amino acids with low steric hindrance, or acidic, basic, polar, hydrophobic and aromatic amino acids in accordance with the table below:

| Low steric hindrance | Ala (A) | Gly (G) | Ser (B) | Thr (T) |
|---|---|---|---|---|
| Acid | Asp (D) | Glu (E) | | |
| Basic | Arg (R) | His (H) | Lys (K) | |
| Polar | Asn (N) | Gln (Q) | | |
| Hydrophobic | Ile (I) | Leu (L) | Met (M) | Val (V) |
| Aromatic | Phe (F) | Tyr (Y) | Trp (W) | |

Thus, for example, the enhanced variant of the present invention or a functional derivative thereof may comprise substitutions equivalent to the substitution P276L described in the previous group, such as the substitutions P276I, P276M or P276V using the classification in the above table. The above interpretation also applies to combinations of substitutions, further, the enhanced phytase variant of the present invention or a functional derivative thereof may comprise other mutations that are not described in this group, preferably substitutions, in particular some that are known in the field. In a particular embodiment, the enhanced phytase variant or a functional derivative thereof comprises a maximum of 40, 35, 30, 25, 20, 15, 14, 13, 12, 11, 10, 9, 8, 7, 6, 5, 4, 3, 2 substitutions or 1 substitution relative to the wild type phytase, in particular relative to SEQ ID No.1.

The term "enhanced variant" means a variant having enhanced properties, in particular thermostability and/or specific activity and/or enhanced expression, relative to the parent phytase. In addition, the enhanced variant of the present invention may have greater resistance to proteolysis by proteases or others. The enhancement to one of more properties of the enhanced phytase variant of the present invention is at least 5%, preferably at least 10%, 20%, 30%, 40%, 50%, 60%, 70%, 80%, 90% or 100%, or by a factor of 2, 5, 10 or 100 compared with the properties of the parent phytase, measured under the same experimental conditions. In a preferred embodiment, said enhancements amount to at least 20%. The thermostability of the phytase may be measured using procedures that are detailed in Example 5. The specific activity of the phytase may be measured using the procedures detailed in Example 4. Phytase expression may be measured using the procedures detailed in Examples 2 and 3.

Visualizing model structures in 3D using software such as swiss-model (worldwideweb expasy.ch) and spdbv v4.01 (GlaxoSmithKline) often means that hypothetical explanations can be constructed by comparison with structural modifications to enzymes that cause changes in activity and/or properties, particularly as regards the possible bonds between adjacent amino acids. When taking a predictive approach, such visualizations also mean that certain residues can be targeted for mutagenesis experiments. As an example, when enhanced thermostability is desired, the targeted residues may be those that can stiffen the secondary structure. Said stiffening may be accomplished in different manners; as an example, the targeted residues may be substituted with a proline residue that conventionally generates fewer rotamers and thus stiffens the secondary structure to which it belongs. In addition, stiffening of the secondary structures may be accomplished by generating new hydrogen bonds and new saline bridges; visualizing model structures in 3D means that residues that can establish such bonds with structurally close residues can be targeted. When enhanced thermostability and/or activity is desired, an approach other than the visualization of 3D models is to modify the charges carried by a residue and the ensuing steric stresses. It is known that in some circumstances the substrate/product of an enzyme participates in stabilizing the 3D conformation of the enzyme and may provide increased thermostability. It is clear that visualizing such model structures in 3D means that residues can be focused upon for enhancing other parameters of the enzyme of industrial interest such as activity, expression or resistance to proteolysis, for example. It is also clear that this approach by visualizing model structures in 3D is a predictive tool allowing mutagenesis strategies to be constructed without in any way guaranteeing any enhancement in enzymatic properties.

The term "expression vector" means that the expression vector may be any type of recombinant vector (in particular a plasmid, virus, etc), enabling the nucleotide sequence of the enhanced variant of the present invention to be expressed. The choice of this expression vector depends on its compatibility with the targeted expression host in which it is transformed or transfected. Said vector may be linear or a closed circle. It may replicate autonomously, i.e. it may be an extrachromosomal entity replication of which is independent of the chromosome of the host containing it, a plasmid, an extrachromosomal element, a mini-chromosome or an artificial chromosome. In contrast, when it is introduced into the host cell, the vector may be integrated into the genome of the host for replication at the same time thereof. Equally, several vectors may be necessary for expression of the enhanced variant of the present invention and may be used simultaneously, as well as a transposon.

The vectors allowing expression of the enhanced variant of the present invention may contain one or more markers that allow easy selection of transformed or transfected host cells. Said selection markers are typically genes the product of which provides their host with an advantage and, for example, produces bacterial resistance to an antibiotic, prototrophy for auxotrophs, resistance to heavy metals, etc. Examples of bacterial selection markers are genes that provide resistance to antibiotics such as ampicillin, kanamycin, tetracyclin and chloramphenicol in particular. Particular examples of markers suitable for selection in yeasts are the genes ADE2, HIS3, LEU2, LYS2, MET3, TRP1 and URA3. Particular examples of markers used in filamentous fungi are amdS (acetamidase), argE (ornithin carbamoyltransferase), bar (phosphinothricin acetyltransferase), hph (hygromycin phosphotransferase), niaD (nitrate reductase), pyrG (orotidin-5'-phosphate decarboxylase), sC (adenyltransferase sulfate) and trpC (anthranilate synthase), in particular. The vectors allowing expression of the enhanced variant of the present invention do not have to contain selection markers.

With autonomous replication, the vector must contain an origin of replication adapted to the host cell. Particular examples of bacterial origins of replication are those of the plasmids pBR322, pUC19, pACYC177 and pACYC184 for replication in *Escherichia coli*, and pUB110, pE194, pTA1060 and pAM[beta] for replication in *Bacillus*. Non-exhaustive examples of origins of replication in yeasts are the 2-micrometer origins of replication ARS1, ARS4, the combination of ARS1 and CEN3 and the combination of ARS4 and CENG. The origin of replication may also contain a mutation that means that it can be sensitive to temperature. Examples of origins of replication for use in filamentous fungi are AMA1 and ANS1 from *Aspergillus nidulans* (Gems et al., 1991, Gene 98:61-67; Cullen et al., 1987, Nucleic Acids Research 15: 9163-75; WO 00/24883).

With integration into the genome of the host cell, the vector must allow its integration by means of the coding sequence for the enhanced variant of the present invention or any other suitable sequence in the vector, via homologous or non-homologous recombination. It may also contain additional nucleic acid sequences to direct its integration into the genome of the host cell. In order to maximize the chances of integration into the genome of the host, the integration sequences must be of sufficient length, such as 100 to 10000 base pairs, preferably 400 to 10000, more preferably 800 to 10000 base pairs. The integration sequences may be coding or non-coding.

The 23 codon "signal" nucleotide sequence present at the 5' end of the gene for *Yersinia intermedia* phytase (denoted in the NCBI by numbers NZ_AALF01000052 and ZP_00832361) and cleaved in the mature form contributes to secretion of the enzyme in its host of origin. The presence of such a sequence is conventional and well known to the skilled person. Changing this sequence and replacing it with a suitable sequence is also a tactic that is well known to the skilled person when expression of the gene under consideration is desired in another organism or in another cellular compartment via a plasmidic vector or other vector selected to suit the desired organism for expression. Thus, said sequence may be replaced by the signal sequence for other genes such as that for PelB, PhoA, OmpA or β-lactamase in particular, for its expression in a prokaryotic host. During expression in a yeast such as *Pichia pastoris*, the signal sequences present at the 5 end of the gene for the phytase of *Yersinia intermedia* may be the signal sequences PHO1 and αfactor respectively from the genes for a phosphatase and the αfactor of that organism. During expression in *Saccharomyces cerevisiae*, the same αfactor signal sequence may be used. During expression in *Yarrowia lypolytica*, the signal sequence present at the 5' end of the gene for the phytase from *Yersinia intermedia* may be the XPR2 signal sequence from the same XPR2 gene of a protease of said organism.

The term "host cell" means that the cell may be prokaryotic or eukaryotic; it may be a gram positive bacterium such as *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis, Bacillus thuringiensis, Streptomyces lividans* or *Streptomyces murinusque* in particular, or a gram negative bacterium such as *Escherichia coli* or *Pseudomonas* sp., for example; this list is not limiting. The present invention also provides a method of the production of a phytase or a variant thereof that is soluble and active in a bacterium, preferably *Escherichia coli*, comprising expression of a nucleic acid encoding the phytase or a variant thereof in a bacterium, preferably *Escherichia coli*, and optionally recovering the phytase so expressed.

The host cell may be a yeast from the genus *Candida, Hansenula, Kluyveromyces, Pichia, Saccharomyces, Schizosaccharomyces*, or *Yarrowia*, in particular. The host cell may preferably be *Saccharomyces carisbergensis, Saccharomyces cerevisiae, Saccharomyces diastaticus, Saccharomyces douglasii, Saccharomyces kluyveri, Saccharomyces norbensis, Saccharomyces oviformis, Kluyveromyces lactis, Pichia pastoris* or *Yarrowia lipolytica.*

The host cell may be a filamentous fungus from the genus *Acremonium, Aspergillus, Aureobasidium, Bjerkandera, Ceriporiopsis, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma*. The host cell may preferably be *Aspergillus awamori, Aspergillus fumigatus, Aspergillus foetidus, Aspergillus japonicus, Aspergillus nidulans, Aspergillus niger, Aspergillus oryzae, Caldariomyces fumago, Fusarium bactridioides, Fusarium cerealis, Fusarium crookwellense, Fusarium culmorum, Fusarium graminearum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulfureum, Fusarium torulosum, Fusarium trichothecioides, Fusarium venenatum, Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenurn, Phanerochaete chrysosporium, Phlebia radiata, Pleurotus eryngii, Thielavia terrestris, Trametes villosa, Trametes versicolor, Trichoderma harzianum, Trichoderma koriingii, Trichoderma longibrachiatum, Trichoderma reesei*, or *Trichoderma viride.*

The host cell may be a mammalian cell such as COS7 or CHO (U.S. Pat. No. 4,889,803; U.S. Pat. No. 5,047,335).

The term "nucleic acid" means DNA (cDNA or gDNA), RNA or a mixture of the two. The nucleic acid may comprise modified nucleotides comprising, for example, a modified bond, a modified puric or pyrimidic base, or a modified sugar. It may be prepared using any method known to the skilled person, including chemical synthesis, recombination, mutagenesis, etc.

The nucleic acid coding for an enhanced phytase variant of the present invention may be optimized in terms of the codons constituting it to maximize its expression in a particular host that differs from its organism of origin. Since the universal genetic code is degenerate, several codons (codon=triplet of nucleotides) exist that code for a given amino acid. These homonymic codons are not used randomly, since the corresponding tRNAs (transfer RNA) do not exist in all cells in the same concentrations. This means that certain codons then have less chance of being expressed in tissues where the corresponding tRNA is rare. This fact, which is well known to the skilled person, is an important parameter to be considered when carrying out expression in a given host that differs from the organism of origin of a particular transgene. Tables of the frequency of use of codons in a particular organism have been published and are well known to the skilled person. Thus, the nucleic acids coding for the enhanced phytase variants of the present invention may have to be optimized in order to promote their expression in a selected production host.

The term "percentage identity" or "identity" between two nucleic acid or amino acid sequences in the context of the present invention means a percentage of nucleotides or amino acid residues that is identical between the two sequences to be compared, obtained after the best alignment, said percentage being purely statistical and the differences between the two sequences being distributed randomly over their entire length. The best alignment or optimum alignment is the alignment for which the percentage identity between the two sequences to be compared, as calculated below, is the highest. Comparisons of sequences between two nucleic acid or amino acid sequences are traditionally carried out by comparing these sequences after having aligned them in an optimized manner, said comparison being carried out in comparison segments or windows to identify and compare local regions with sequence similarity. As well as carrying it out manually, sequences may be optimally aligned for comparison using the Smith and Waterman (1981) local homology algorithm (Ad. App. Math. 2: 482), using the Neddleman and Wunsch local homology algorithm (1970) (J. Mol. Biol. 48: 443), using the Pearson and Lipman similarity search method (1988) (Proc. Natl. Acad. Sci. USA 85: 2444), or employing software programs using those algorithms (GAP, BESTFIT, FASTA and TFASTA in the Wisconsin Genetics Software Package, Genetics Computer Group, 575 Science Dr., Madison, Wis.). The percentage identity between two nucleic acid or amino acid sequences is determined by comparing these two aligned sequences in an optimized manner by means of a comparison window in which the region of the nucleic acid or amino acid sequence to be compared may include additions or deletions compared with the reference sequence for optimized alignment between those two sequences. The percentage identity is calculated by determining the number of identical positions for which the nucleotide or the amino acid residue is identical for the two sequences, by dividing this number of identical positions by the total number of positions in the comparison window and by multiplying the result obtained by 100 to obtain the percentage identity between those two sequences. Thus, amino acids that are conserved or equivalent to those present in the enhanced phytase variant of the present invention may be discerned in phytases from other organisms. Thus, the enhancement provided by the selected substitutions in the enhanced phytase variant of the present invention may be discerned by carrying out an equivalent substitution in a phytase for an organism other than that from which the phytase of the present invention originates. Clearly, such equivalent substitutions fall within the purview of the present invention.

The enhanced phytase variant of the present invention may be used in the reactions and methods mentioned above in a purified or partially purified form. Purification of the enhanced phytase variant of the present invention may be basic and in particular carried out by lysis and filtration of the contents of flasks or production containers and/or by centrifuging steps, and/or by successive selective precipitations using ammonium sulfate and/or by evaporation. Said basic procedures can be used to obtain fractions of the enhanced phytase variant of the invention exhibiting a large increase in specific activity. Purification of the enhanced variant of the invention may be complete and require various steps that are well known to the skilled person, in particular chromatography (ion exchange, affinity, hydrophobic, size exclusion), or electrophoresis (preparative, by isoelectric concentration) [Protein Purification, J. C. Janson and Lars Ryden, VCH Publishers, New York, 1989].

The purified or partially purified fraction of the enhanced phytase variant of the present invention may be used in the reactions and methods mentioned above, in the immobilized or non-immobilized form. Methods of immobilizing the enhanced variant of the present invention on organic or inorganic supports are well known to the skilled person. These supports may in particular be polyacrylamides, agaroses, celluloses, sephadexes or dextrans, porous glass beads, or aluminum or titanium hydroxides.

The term "composition" generally means a composition comprising at least one enhanced phytase variant whose sequence is SEQ ID No.1 with the selected substitution or substitutions of the present invention. It also provides any solid, liquid or gaseous mixture comprising a certain percentage of at least one enhanced phytase variant of the present invention. It also provides mixtures containing one, two, three, four, five or ten enhanced phytase variants of the present invention.

In general, the compositions containing the phytases are liquid or so-called "dry" compositions.

Liquid compositions do not have to contain anything other than highly purified phytase. However, stabilizers such as glycerol, sorbitol or monopropylene glycol may be added. Said composition may also contain other additives such as salts, sugars, preservatives, pH buffers, proteins and phytate. Typically, the liquid compositions are aqueous compositions or oil-based suspensions. The liquid compositions may be added to the food before or after an optional granulation step.

So-called "dry" compositions may be compositions that are dried by freezing, spraying, or they may be extruded dry compositions; under such circumstances, said composition does not have to contain anything other than the enzyme in its dry form. The dry compositions may also be granules that can be mixed or are ready to be mixed with a food component, or to form a pre-mix component. The size of the enzyme granules is preferably compatible with that of the other components of the mixture. This represents a safe and practical way of incorporating one or more enzymes into the food.

As an example, a stable enzyme formulation may be prepared by spraying a liquid phytase mixture onto a component such as soya meal then drying the assembly. The reduction in the moisture content and binding interactions of the phytase with the component protect the enzyme from external environmental factors such as the extreme temperatures employed during manufacture of the food component. In addition, presenting the phytase preparation in the dry form may improve its stability by reducing the activity of potential proteolytic enzymes that may be present in trace amounts at the end of the liquid fermentation steps during the production method. The dry phytase preparation may, for example, be used as a food supplement in the poultry and pig production industry.

Starting from a dry enzyme preparation, granules are prepared using agglomeration techniques that are well known to the skilled person, in a mixer in which a filler material and the enzyme are co-agglomerated to form granules. The granules are prepared from matrices onto which the enzyme may be absorbed or onto which a layer of enzymes may be applied. Typical materials that can serve as a matrix are salts such as disodium sulfate. Other potential matrices may be based on talc, clay, magnesium silicate, aluminum silicate or cellulose fibers. Optionally, binding agents such as dextrins may be included in the granules.

Entraining agents may be included, in any form of the following components: starch, manioc, potato, rice, wheat, corn etc. Salts may also be added.

Optionally, the granules may be coated with specifically dedicated mixtures, in particular hydrophobic mixtures, based on palm nut oil, beef suet and, if necessary, other additives such as calcium carbonate or clay.

Further, the phytase preparation may contain other agents such as colorants, aromatic compounds, stabilizers, vitamins, minerals as well as other enzymes or mixtures of enzymes having advantageous properties. This is particularly true for pre-mixes.

The term "food additive" means a component that is practically pure or a composition containing several components intended to be added to a food. In particular, said additive is intended to become a fully-fledged component of said food and is intended to affect, modify or enhance one or more properties of said food. Thus, a phytase preparation used as a food additive means a phytase that is not a natural component of the food to which it is added or that is not present in that food in its natural concentration, or that is added separately from the other components of the food, alone or in association with other food additives. Typically, a food additive contains several components such as vitamins, minerals, entraining agents, excipients, other enzymes or mixtures of enzymes with advantageous properties.

The term "phytase preparation as a food additive ready for use" or "phytase as a ready to use food additive" means a food additive that is not produced in situ in the food or the animal feed. Such a phytase or preparation may be given directly as a food to humans or to animals, preferably directly after mixing with the other constituents of said food. As an example, a food additive in accordance with this aspect of the present invention is combined with other compounds in order to produce a food. These other compounds include one or more other enzymes, preferably thermostable, vitamin-containing food additives, mineral food additives, or amino acids as food additives. The result of this mixture or this combination of compounds may be mixed, in appropriate proportions, with other components such as protein or cereal supplements to form the final food. The methods of manufacturing said food may be carried out using any apparatus that is well known to the skilled person, such as a double granulation machine, a steam granulator, an expander or an extruder.

The term "phytase preparation" or "phytase composition" as used in the present invention means preparations of compositions that contain a significant quantity of at least one enhanced phytase variant of the present invention and one or more other enzymes having advantageous properties for the preparation of food. Such enzymes may appear on the following non-exhaustive list: alpha-galactosidases, beta-galactosidases, in particular lactases, other phytases, beta-glucanases, in particular endo-beta-1,4-glucanases and endo-beta-1,3(4)-glucanases, cellulases, xylosidases, galactanases, in particular arabinogalactan-endo-1,4-beta-galactosidases and arabinogalactan-endo-1,3-beta-galactosidases, endoglucanases, in particular endo-1,2-beta-glucanase, endo-1,3-alpha-glucanase, and endo-1,3-beta-glucanase, enzymes that degrade pectins, in particular pectinases, pectinesterases, pectin lyases, polygalacturonases, arabinanases, rhamnogalacturonases, rhamnogalacturonan-acetyl-esterases, rhamnogalacturonan-alpha-rhamnosidase, pectate lyases, alpha-galacturonisidases, mannanases, beta-mannosidases, mannan-acetyl-esterases, xylan-acetyl-esterases, proteases, xylanases, arabinoxylanases and lipolytic enzymes such as lipases, phospholipases and cutinases.

Supplementation of the animal feed additive in accordance with the present invention may be carried out before or simultaneously with a meal. Preferably, supplementation is carried out at the same time as the meal.

An effective quantity of phytase that may be added to food is approximately 10 PPU/kg to 20000 PPU/kg of food; preferably in the range 10 PPU/kg to 15000 PPU/kg; more preferably in the range 10 PPU/kg to 10000 PPU/kg, in particular 100 PPU/kg to 5000 PPU/kg, particularly 100 PPU/kg to 2000 PPU/kg of food.

The scope of the invention also includes the use of an enhanced phytase variant of the present invention in the manufacture of foods intended for human or animal consumption. Grain or flour intended for human food may be treated with the phytase to reduce their phytate content, allowing an increase in the nutritional value of said products by increasing the availability of essential minerals such as iron, calcium and zinc, for example. Beyond the nutritional value, such a treatment with phytase may enhance the efficiency of production of that food. As an example, adding phytase to white soya flakes during the soya protein extraction process may enhance the yield and quality of the extracted proteins. The phytase is active during the manufacture of the food, but not in the final product. This is particularly true when producing and baking dough for baked items. Similarly, in the production of animal feed, soya or rapeseed grain may be pre-treated with phytase before their final manufacture and/or conditioning. Such pre-treatment means that anti-nutritional elements such as phytate can be degraded and the quality of the nutritional value of the food in question can be enhanced. The phytase may then optionally still be active in the digestive tract of the animals after ingesting the food.

The scope of the invention also encompasses the use of an enhanced phytase variant of the present invention as an agent facilitating food transformation. In particular, the phytase of the present invention may be used as a supplement in human food to facilitate digestion. As an example, one or more tablets containing a suitable quantity of phytase may be ingested by an individual before eating in order to provide that individual's digestive tract with an active enzyme. The benefit of ingesting phytase is particularly remarkable when eating food that cannot be treated with the phytase during its manufacture.

The phytase of the present invention may advantageously be used with mono- or polygastric animals, in particular young cattle. Diets intended for fish and crustaceans may also be treated with the phytase in order to improve the conversion yields between the food supplied and growth of the animals, and also to reduce the quantities of phosphate excreted in intensive production systems. The food treated in accordance with the present invention may be provided to poultry (turkeys, ducks, geese, partridge, hens, broilers), to pigs, horses, cattle, sheep and goats, dogs or cats. It is of particular application to poultry and pigs, including but not being limited to hens, broilers, turkeys, ducks and geese.

The phytase of the present invention is used to produce novel combinations of food ingredients or food with advantageous qualities. As an example, it may be used to produce food with a reduced inorganic phosphate content. This quantity is adjusted as a function of the quantity and activity of the added phytase present in the final food, or active in one of the food ingredients forming part of the composition of the final food. Preferably, such a food can contain ingredients such as micro-nutrients, vitamins, amino acids and effective and optimized quantities of phytase and inorganic phosphate such that the quantity of phytase is in the range 50 to 20000 units of phytase per kilo of food and the quantity of inorganic phosphate is less than 0.45%. Preferably, these two quantities are in the range 100 to 10000 units of phytase per kilo of food and less than 0.225% of inorganic phosphate; more preferably in the range 150 to 10000 units of phytase per kilo of food and less than 0.15% of inorganic phosphate; still more preferably in the range 250 to 20000 units of phytase per kilo of food and with no added phosphate. These novel combinations are of broad interest, such as in reducing phosphate discharges into the environment and optimizing the conversion yields between the food supplied and animal growth, which is particularly sought-after in intensive stock farming.

BRIEF DESCRIPTION OF THE TABLES AND DRAWINGS

Figure 2:
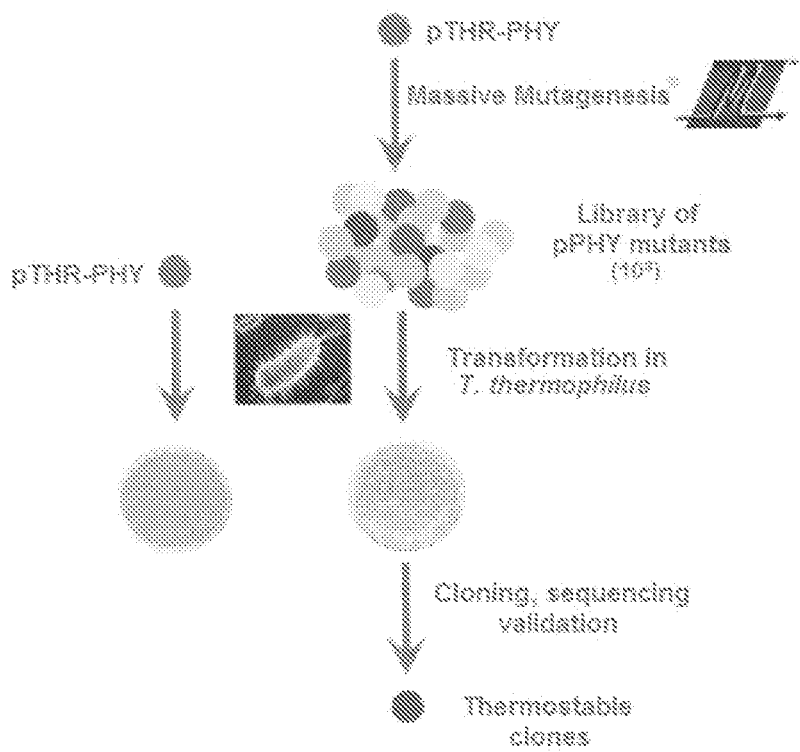
Figure 3:
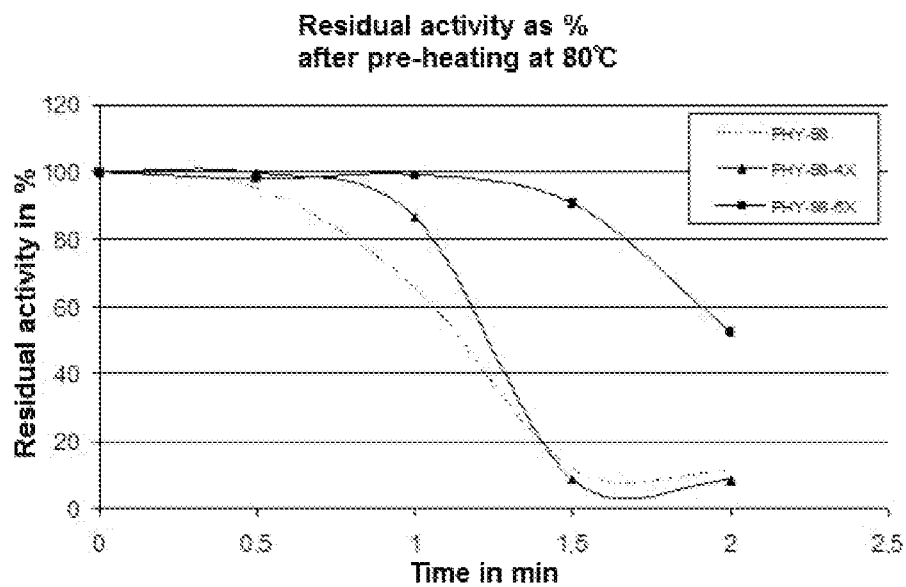
Figure 4:
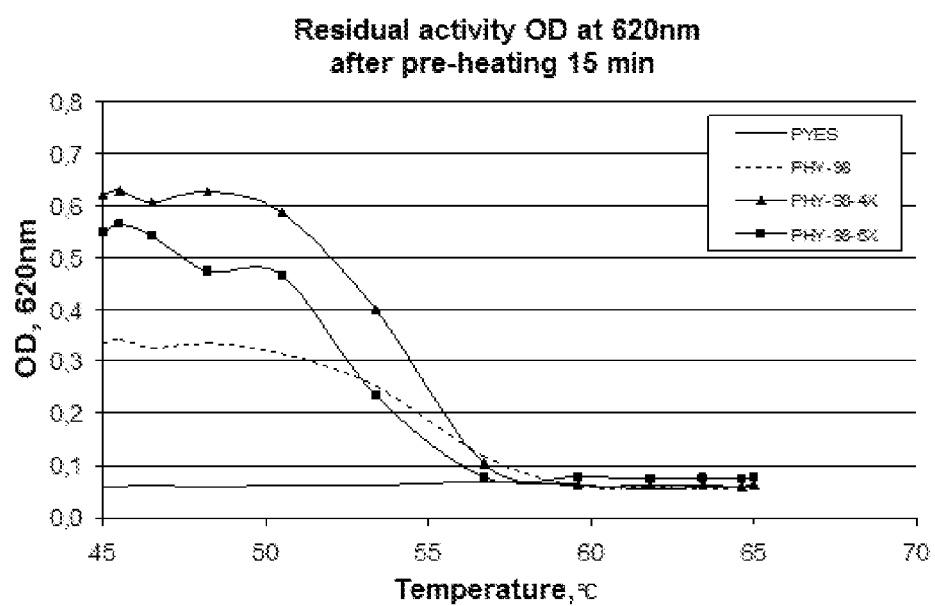
Figure 5:
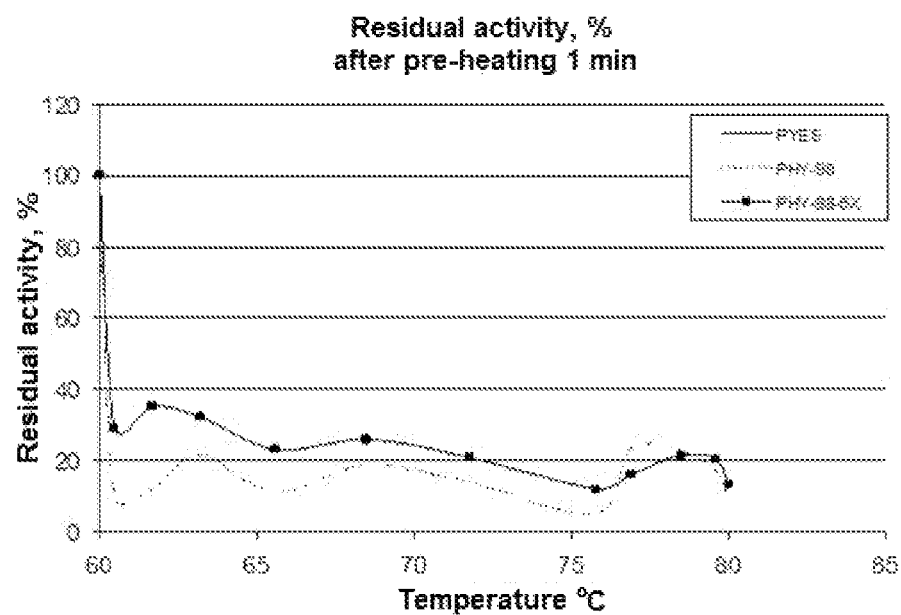
Figure 6A:
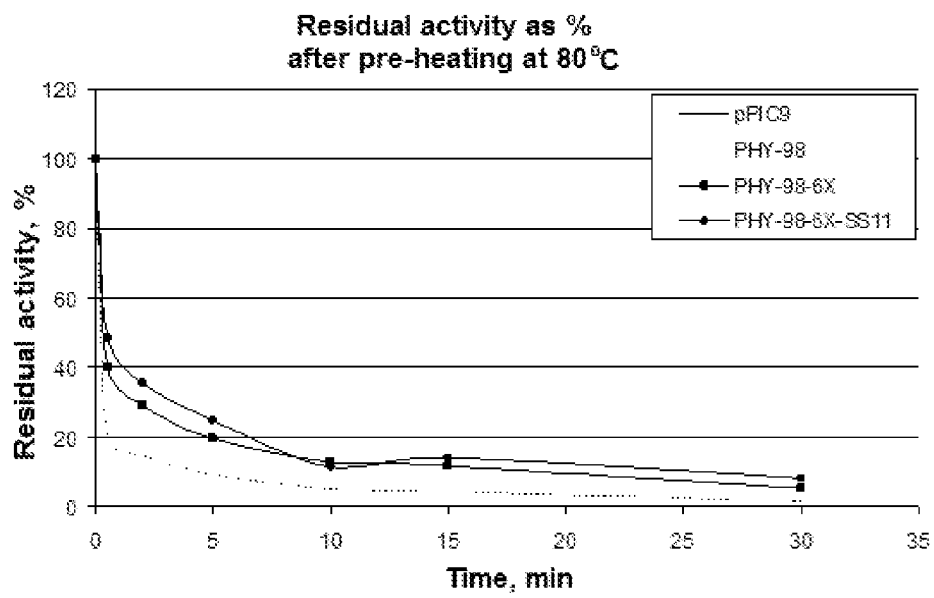
Figure 6B:
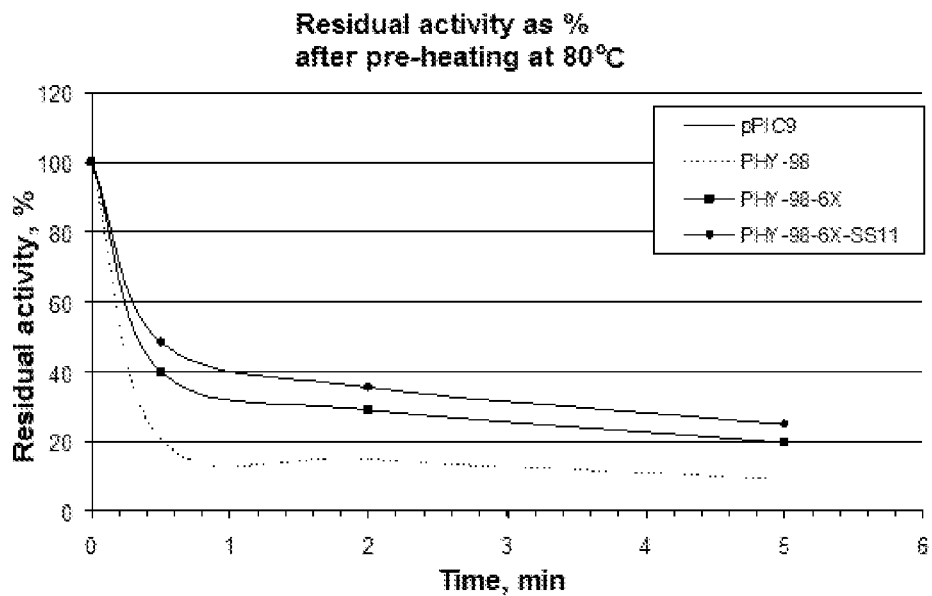
Figure 7:
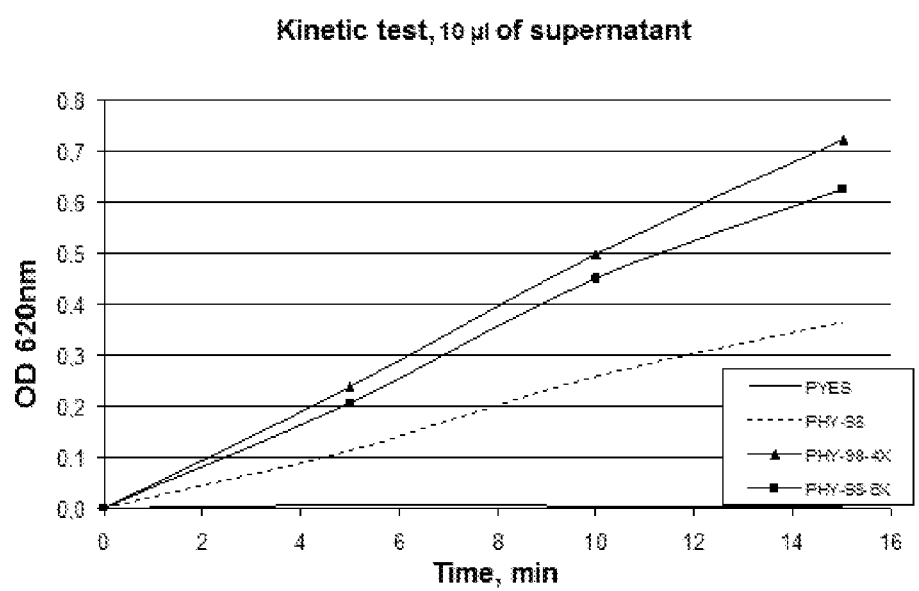
Figure 8:
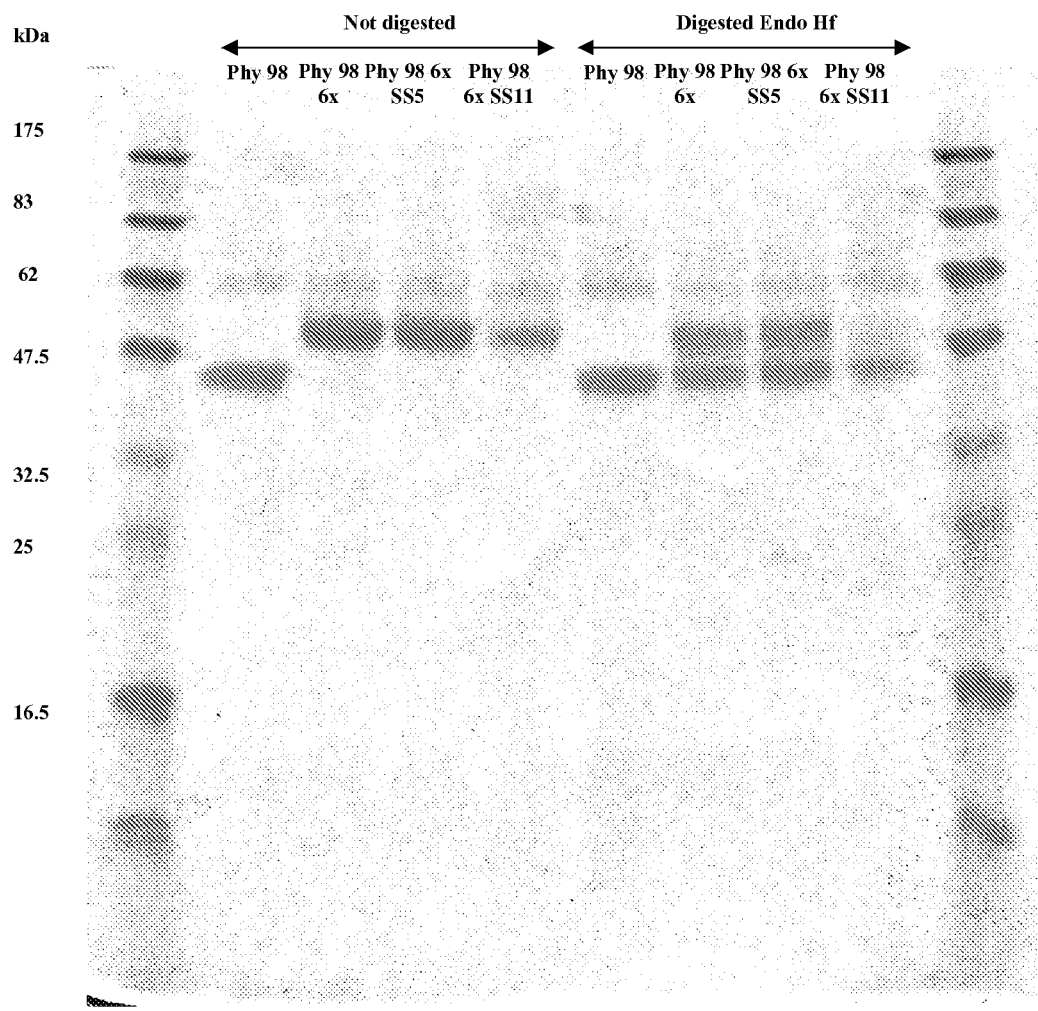

The present invention is described below in more detail in the following examples, which are in no way limiting in nature, with the aid of the accompanying figures and tables:

Table 1: Mutants isolated using the THR™ approach;

Table 2: List of mutants with an additional glycosylation site classified as a function of their percentage accessibility to the respective solvents;

Table 3: List of pairs of mutations allowing the addition of additional disulfide bridges;

Table 4: 80%-20% activity extinction coefficients various mutants:

Table 4A: 80%-20% activity extinction coefficients for the mutants K210S, Y268E and Q292P;

Table 4B: Details of data for calculating the 80%-20% activity extinction coefficient of the mutant K210S;

Table 4C: 80%-20% activity extinction coefficients for the mutants T142N, A177T and Q326T;

Table 4D: 80%-20% activity extinction coefficients for the G274C/N316C mutant;

Table 5: Lists of mutants targeting enhanced activity:

Table 5A: List of positions targeted by a distance of 10 Angstrom or less about the catalytic enzyme site;

Table 5B: List of substitutions targeting an enhancement to the activity characterized in a first series of experiments;

FIG. 1: Degradation of phytate by a phytase;

FIG. 2: Principle of THR™ technique;

FIG. 3: Measurement of residual activities of the mutants PHY-98-4X and PHY-98-6X produced by *Saccharomyces cerevisiae* after pre-heating for 0 to 2 minutes at 80° C.;

FIG. 4: Measurement of residual activities of the mutants PHY-98-4X and PHY-98-6X produced by *Saccharomyces cerevisiae* after pre-heating for 15 minutes at temperatures of 45° C. to 65° C.;

FIG. 5: Measurement of residual activities of the mutants PHY-98-4X and PHY-98-6X produced by *Saccharomyces cerevisiae* after pre-heating for 1 minute at temperatures of 60° C. to 80° C.;

FIG. 6A: Measurement of residual activities of the mutants PHY-98-6X and PHY-98-6X-ss11 produced by *Pichia pastoris* after pre-heating for 0 to 30 minutes at 80° C.;

FIG. 6B: Measurement of residual activities of the mutants PHY-98-6X and PHY-98-6X-ss11 produced by *Pichia pastoris* after pre-heating for 0 to 5 minutes at 80° C.;

FIG. 7: Measurement of the relative activities of the mutants PHY-98-4X and PHY-98-6X, compared with the enzyme of origin PHY-98, produced by *Saccharomyces cerevisiae*, as a function of time;

FIG. 8: 12% SDS-PAGE gel of production supernatants for various mutants expressed by *Pichia pastoris*, digested or not digested by the endoglycosidase Hf.

DETAILED DESCRIPTION OF THE INVENTION

Examples

Example 1

Obtaining Enhanced Phytase Variants from *Yersinia intermedia*

Plasmidic Constructs:

Producing enhanced phytase variants of the present invention required the construction of various plasmidic vectors that were capable of carrying out the directed mutagenesis experiments necessary in order to obtain libraries of variants or mutants as well as for the expression of said mutants in various screening or production hosts.

Constructs in pET25b:

Using molecular biological techniques that are well known to the skilled person, the ORF (Open Reading Frame) ZP_00832361 corresponding to the sequence NCBI ATCC 29909 and to the corresponding nucleotide sequence NZ_AALF01000052, region: 1889 ... 3214 was cloned into the plasmidic vector pET25b. Before cloning, the original signal sequence (first 23 amino acids) was deleted from the ORF and replaced by the signal sequence for the phytase of *Escherichia coli*. This signal sequence for the phytase of *Escherichia coli* had been cloned into the vector pET25b in order to optimize expression of the phytase from *Yersinia intermedia* in *E. coli*. The vector pET25b could also be used to express the protein of interest in the form of a fusion protein with a "6H is tag" facilitating isolation and/or purification of the protein of interest using methods that are well known to the skilled person. This vector containing the phytase from *Yersinia intermedia* fused with the signal sequence of the phytase from *E. coli* was transformed in a BL21 (DE3) *E. coli* strain from which the AppA gene coding for the endogenous phytase of *E. coli* had been deleted.

Constructs in pNCK:

The ORF of ZP_00832361 was cloned into the vector pNCK using molecular biological techniques that are well known to the skilled person. This vector can be used to express, in a thermophilic microorganism *Thermus thermophilus*, a fusion protein between the protein of interest and a thermostable kanamycin resistance gene using the method described in patent application WO 2006/134240 and corresponding to Biométhodes' THR™ technique.

Constructs in pYES2:

The ORF of ZP_00832361 was cloned into the vector pYES2 using molecular biological techniques that are well known to the skilled person. This vector, containing the signal peptide for the phytase of *Aspergillus niger* in the 5' position of the ORF ZP_00832361, allowed expression of the phytase from *Yersinia intermedia* by *Saccharomyces cerevisiae*.

Constructs in pPIC9:

The ORF of ZP_00832361 was cloned into the vector pPIC9 using molecular biological techniques that are well known to the skilled person. This vector, containing the signal peptide of the αfactor of *Pichia pastoris* (Invitrogen) in the 5' position of the ORF ZP_00832361, allowed expression of the phytase from *Yersinia intermedia* by *Pichia pastoris*.

Construction of Libraries of Mutants in pNCK, Screening and Obtaining Enhanced Variants:

Several libraries of mutants of the phytase from *Yersinia intermedia* were created using Biométhodes' Massive Mutagenesis® technique described in U.S. Pat. No. 7,202,086 or in Saboulard et Si (Biotechniques, 2005 September 39(3): 363-8). Briefly, mutagenic oligonucleotides were synthesized to produce phytase mutants on each of the amino acids constituting the enzyme. The libraries of mutants were constructed from the vector pNCK containing the gene of the phytase using the Massive Mutagenesis® protocol described in U.S. Pat. No. 7,202,086 or in Saboulard et al (Biotechniques, 2005 September 39(3): 363-8), then transformed and amplified in the *Escherichia coli* strain DH10B. The mutants of the phytase contained in these libraries were then screened using the THR™ technique described in patent application WO 2006/134240, the principle of which is summarized in FIG. 2. The possibility offered by the system for selecting, in a single step, a very large number of mutant molecules means that highly diverse libraries can be worked with. Such a library, targeting all of the residues of the protein, approximately $10^8$ clones, was constructed using Massive Mutagenesis®.

Briefly, the libraries of mutants were transformed in cultures of *Thermus thermophilus* that had been rendered competent. The transformants were set to grow in liquid medium at 70° C. to produce pre-cultures that were then spread onto a solid medium containing stringent concentrations of kanamycin of the order of 25 μG/mL. After incubating for 48 hours at 70° C., only the mutants with a protein structure that resisted the selection temperature and that were folded correctly could allow functional folding of the thermostable kanamycin-resistant gene and thus could grow in the presence of kanamycin. Using this approach, various mutants were isolated, and their plasmidic DNA was isolated and sequenced. The various mutants revealed a total of 138 substitutions in the 89 positions shown in Table 1. The various substitutes were introduced individually into the phytase cloned into the plasmidic vector pET25b in order to be expressed in *Escherichia coli* and characterized in more detail as regards their activity and their thermostability. Example 4 details the protocols for measuring the activity used and Example 5 details the protocols for characterizing the residual activity of the mutants as a function of temperature. A first series of experiments was able to identify at least 5 mutants with an enhanced thermostability relative to the wild type enzyme. Of these, 3 mutants respectively contained substitutions on the amino acids K210, Y268 and Q292, particularly the substitutions K210S, Y268E and Q292P. These mutants had an 80%-20% residual activity extinction coefficient of respectively 1.75, 1.98 and 2.30 as can be seen in Table 4A. These indices were calculated by the ratio between the differences in temperatures allowing firstly 80% of residual activity to be retained and secondly 20% of residual activity to be maintained for the various variants compared with the wild type enzyme. Details of the calculation of this index are shown for the mutant K210S in Table 4B.

Visualizing model structures in 3D using software such as the swiss-model (worldwideweb expasy.ch) and spdbv v4.01 (GlaxoSmithKline) means that certain explanations can be advanced concerning the increases in thermostability obtained for the 3 mutants mentioned above. K210 is a potentially solvent-accessible residue located in a secondary "sheet"-like structure, possibly involved in bonding and/or interaction with the substrate (phytate) or the products derived from the reaction. K210 thus seems to be an important residue in particular because of its positive charge and its large volume, which could generate steric and electrostatic constraints as regards access of the substrate to or egress of products from the active site. The loss of this positive charge in the K210S substitution and modification of the associated spatial constraint could thus in general perturb the reaction (access of substrate+egress of products+solvation of the active site cavity) and modify the kinetic constants thereof, more particularly the apparent Kms for the various substrates generated during the reaction. In some circumstances, it is known that the substrates/product could participate in stabilizing the 3D structure of the protein and provide increased thermostability. It might be envisaged that this substitution could, for example, facilitate positioning of the substrate by increasing the number of conformers tolerated in the active site and/or could also facilitate evacuation of the phosphates liberated during the reaction, preventing them from being too numerous in the cavity of the active site, which presence could clearly perturb the enzyme-substrate complex and destabilize the whole structure. Y268 is a potentially solvent-accessible residue located in the secondary "loop" type structure. By modeling the Y268E substitution using the software mentioned above, it can be established that the number of potential hydrogen bonds with structurally close residues (with the CO peptide function of the Q143 residue for example) are increased, but also that this substitution could produce an additional saline bridge, in particular with K146. Overall, the region in question becomes stiffer, which could explain the observed gain in thermostability. Q292 is also a potentially solvent-accessible residue located in a secondary "loop" type structure. Substitution by a proline residue is a relatively conventional engineering approach in this type of secondary structure with poor conservation. This type of residue generates few rotamers, and as a consequence stiffens the secondary structure in which it is located and thus can sometimes result in increased thermostability that could thus bring about the substitution Q292P.

Construction of Mutants with Additional Glycosylation Sites

Certain post-translational modifications such as glycosylations have been described as being protein stabilizers. The signals for N-glycosylations in a protein sequence are NxT or NxS. Such sites were introduced into the phytase of *Yersinia intermedia* cloned into the vector pYES2 either using the protected Biométhodes Massive Mutagenesis® technique mentioned above or using a mutagenesis technique that is well known to the skilled person, such as overlapping PCR, by introducing a T residue at the +2 position relative to a residue N present in the phytase of *Yersinia intermedia* or by introducing a residue N at the −2 position relative to an S or T residue. The positions into which the glycosylation sites were introduced are classified as a function of their percentage accessibility to solvents (% ASA) using the software available at: worldwideweb mobyle.rpbs.univ-paris-diderot.fr/cgi-bin/portal.py?from=ASA (T. J. Richmond, Solvent accessible surface area and excluded volume in proteins. J. Mol. Biol, 178, 63-89 (1984). Preferably, 22 substitutions on residues with a percentage accessibility to solvents of >35% were selected. More preferably, 10 substitutions on residues with a percentage accessibility to solvents of >70% were selected. These different variant constructs allowing the addition of glycosylation sites are summarized in Table 2 as a function of their respective percentage accessibility to solvents.

The mutant constructs were transformed in *Saccharomyces cerevisiae* and characterized in more detail as regards their activity and thermostability. Example 5 details the protocols for characterizing the residual activity of the mutants as a function of temperature. A first series of experiments was able to identify several mutants with an additional glycosylation site having enhanced thermostability compared with the wild type enzyme. These mutants contain substitutions on the amino acids T142, A177 and Q326 characterized by a percentage accessibility to solvents of >70%. More particularly, the substitutions on said amino acids are T142N, A177T and Q326T. These mutants have a respective 80%-20% residual activity extinction coefficient of 1.62, 1.62 and 1.52, as shown in Table 4C. These indices were calculated from the ratio between the differences in temperatures allowing firstly 80% of the residual activity and secondly 20% of the residual activity to be retained for the various variants compared with the wild type enzyme. Details of the calculations for this index are shown in Table 4B for the mutant K210S.

Construction of Mutants Having Additional Disulfide Bridges

Several pairs of residues were identified as regards their distance and orientation compatible with the formation of a disulfide bridge and replaced with cysteine residues. These pairs were identified by visualizing model or homologous structures of phytases in pdb format using a Swisspdb Viewer (GlaxoSmithKline) type program, taking into account optimized distances between residues and orientation of the side chains thereof. Using this approach, 12 pairs of residues located at approximately 2 Angstrom were selected and are listed in Table 3.

The above residues were introduced into the phytase from *Yersinia intermedia* cloned into the vector pYES2, either using the protected Biométhodes Massive Mutagenesis® technique as mentioned above or using a mutagenesis technique that is well known to the skilled person such as overlapping PCR. The mutant constructs were transformed in *Saccharomyces cerevisiae* and characterized in more detail as regards their activity and thermostability. Example 5 details the protocols for characterizing the residual activity of mutants as a function of temperature. A first series of experiments was able to identify one mutant with an additional disulfide bridge site and enhanced thermostability. This mutant contains two substitutions on the residues G274 and N316, more particularly the substitutions G274C and N316C. This mutant had an 80%-20% residual activity extinction coefficient of 2.33, as shown in Table 4D. This index was calculated by the ratio between the differences in temperatures allowing firstly 80% of the residual activity and secondly 20% of the residual activity to be retained for the variant SS11 compared with the wild type enzyme. Details of the calculations for this index for the mutant K210S are shown in Table 4B.

Construction of Mutants Targeting Enhanced Activity:

Several residues were targeted in order to identify mutants having an enhanced activity. These residues were identified by visualizing model or homologous structures of phytases in the pdb format using a Swisspdb Viewer (GlaxoSmithKline) type program. The criterion for selection that was selected was: residues located at a distance of 10 Angstrom or less around the catalytic site of the enzyme. Using this approach, 76 positions were selected and are listed in Table 5A. Complete diversity by using the oligonucleotides NNS was introduced at these positions into the phytase of *Yersinia intermedia* cloned into the pYES2 vector, either using the protected Biométhodes Massive Mutagenesis® technique as mentioned above or using a mutagenesis technique that is well known to the skilled person, such as overlapping PCR. Thus, for each of the positions listed in Table 5A, the mutants individually comprising one of the 19 possible substitutions from the list of 20 existing amino acids were constructed; using the standard single letter code, these 20 amino acids are: A, R, N, D, C, E, Q, G, H, I, L, K, M, F, P, S, T, W, Y and V. The mutant constructs were transformed in *Saccharomyces cerevisiae* and characterized in more detail as regards their respective activity and thermostability. Example 5 details the protocols for characterizing the residual activity of the mutants as a function of temperature. A first series of experiments allowed 14 mutants containing the substitutions listed in Table 5B to be characterized.

Combination of Enhancements:

The various approaches employed meant that the thermostability and/or activity and/or proteolysis resistance gains could be accumulated by screening and characterizing the various mutants in each of the approaches: THR™, adding glycosylation sites, adding disulfide bridges and targeting activity. A first series of experiments was used to construct several mutants combining the thermostability enhancements obtained by screening libraries using THR™, adding new glycosylation sites and adding disulfide bridges. These mutants were constructed using the protected Biométhodes Massive Mutagenesis® technique mentioned above. Several mutants were constructed comprising combinations of substitutions: G274C+N316C, T142N+A177T+Q326T, K210S+Y268E+Q292P, D140F+Y268E+Q292P, F167N+Y268E+Q292P, T142N+A177T+K210S+Q326T, T142N+A177T+K210S+Y268E+Q292P+Q326T, T142N+A177T+K210S+Y268E+Q292P+Q326T+G274C+N316C. The mutant constructs were transformed in *Saccharomyces cerevisiae* and characterized in more detail as regards their activity and their thermostability. Example 5 details the protocols for characterizing the residual activity of mutants as a function of temperature. FIGS. 3 to 7 show the results of characterizations of some of these mutants, in particular the mutants PHY-98-4X, PHY-98-6X and PHY-98-6X-SS11 respectively containing combinations of mutations T142N+A177T+K210S+Q326T, T142N+A177T+K210S+Y268E+Q292P+Q326T and T142N+A177T+K210S+Y268E+Q292P+Q326T+G274C+N316C, the positions being indicated in SEQ ID No.1. Three bacterial strains respectively containing the enzyme of origin PHY-98 and the mutants PHY-98-6X and PHY-98-6X-SS11 mentioned above, cloned into the plasmidic vector pYES2 as described above, form the subject matter of a deposit of biological material under respective references CNCM I-4172, CNCM I-4173 and CNCM I-4174, on Jun. 24, 2009. These various mutants may act as a basis for adding one or more additional substitutions deriving from various selective approaches and show one/more enhancements in activity/thermostability in order to create novel combinations of mutations accumulating the enhancements or demonstrating synergistic effects in the enhancements due to these novel combinations of mutations.

Example 2

Expression of Enhanced Variants of the Phytase from *Yersinia intermedia* in *Saccharomyces cerevisiae*

The plasmid pYES2 containing the enhanced phytase variant from *Yersinia intermedia* as described above was transformed by electroporation in the yeast strain *Saccharomyces cerevisiae* ΔPho4 and the transformants were selected on SD-U solid medium. Several clones were pre-cultured in liquid SD-U medium overnight at 30° C., with agitation. Said pre-cultures allowed more culture to be seeded in 2% YP Galactose production medium. They were produced overnight at 30° C., with agitation.

Example 3

Expression of Enhanced Variants of the Phytase from *Yersinia intermedia* in *Pichia Pastoris*

The plasmid pPIC9 containing the enhanced phytase variant from *Yersinia intermedia* as described above was transformed in cells of *Pichia pastoris* that had been rendered competent. After selecting colonies containing the plasmid, one colony was grown for 16 hours at 28° C., with agitation, in 50 mL of BMG medium to form a pre-culture. The production of variants was controlled by using different induction times in 0.5% methanol depending on the desired quantity of said variant. Before induction, the optical density (OD) of the pre-cultures was measured at 600 nm; for induction, optimized ODs of 2 to 60D units were required. The pre-cultures were then centrifuged and re-suspended in BMM medium containing 0.5% methanol at an initial OD in the range 1 to 30 ODu/mL depending on the envisaged induction time: 1 ODu/ml, for 96 hours of induction, 6 ODu/mL for an induction of 72 hours and 30 ODu/ml, for an induction of 48 hours. 100% methanol was added every 24 hours to give a final concentration of 0.5%. These production procedures were employed for Erlenmeyer flask production procedures adapted to volumes of 10 mL to 200 mL.

For higher volumes, production was carried out in a 5 L to 50 L bioreactor adapted to production volumes of 2 L to 20 L. The type of bioreactor used (Applikon) could automatically monitor yeast growth by carrying out regular measurements of the optical density at 600 nm and the oxygen pressure ($pO_2$), optimizing maintenance of the induction conditions with methanol. The procedure used was adapted from the protocol for fermentation in *Pichia pastoris* from Invitrogen ("*Pichia* expression kit; a manual of methods of expression of recombinant proteins in *Pichia pastoris*" • Version H dated 11 Jan. 2002). FIG. 8 shows a 12% SDS-PAGE gel of production supernatants for various mutants expressed by *Pichia pastoris*, digested or otherwise by the endoglycosidase Hf (New England Biolabs P0703). The gel tracks denoted Phy 98, Phy 98 6x and Phy 98 6x SS11 correspond to 10 µG of production supernatants from the molecules PHY-98, PHY-98-6X and PHY-98-6X-SS11 described in Example 1. The mutant Phy 98-6X-SS5 is a mutant containing the substitutions L52C+L99C+T142N+A177T K2105 Y268E+Q292P+Q326T. The Phy98 tracks show the migration profile for wild type phytase of *Yersinia intermedia*, not glycosylated, since it does not have the potential N-glycosylation sites NxS/T; this is illustrated by the absence of differences in migration after digestion with the endoglycosidase Hf. The tracks Phy 98 6x, Phy 98 6x SS5 and Phy 98 6x SS11, in the absence of digestion by the endoglycosidase Hf, show the migration profiles of mutant phytases with high molecular masses due to respective glycosylation of the mutants. This glycosylation is shown, after digestion with the endoglycosidase Hf (tracks denoted "digested Endo Hf"), by a return of the migration profile for the various mutants towards that of the wild type phytase even if digestion by the endoglycosidase may be incomplete in some circumstances.

Example 4

Measurement of the Activity of Enhanced Phytase Variants from *Yersinia intermedia*

The activity of variants of the phytase from *Yersinia intermedia* as well as the activity of the protein of origin used as the control were measured using a colorimetric test measuring the phosphate liberated in the presence of a solution of phytate used as the substrate. In brief, 40 µL of supernatant from the test sample (diluted or not in a sodium acetate buffer) or 40 µL of a calibrating solution of a phosphate were mixed with 40 µL of phytate (20 g/L). The reaction was incubated conventionally for 15 minutes at 37° C. The reaction was stopped with 80 µL of 0.5 M NaOH or 20% TCA. 60 µL of the total volume of the reaction of 160 µL was transferred to be revealed with 60 µL of a Fe—Mo solution. The revealing reaction was left for 15 minutes in the dark before being read in a spectrophotometer at 620 nm. All of the reaction solutions were produced using WFI phosphate-free water. The reaction buffer was a sodium acetate buffer, 0.25 M, pH 4.5. The substrate used was a phytate solution produced in the above reaction buffer from a 200 g/L stock solution. The revealing solution was formed extemporaneously using 4 volumes of Mo solution mixed with 1 volume of Fe solution. The Mo solution was a solution of 0.012 M molybdate and the Fe solution was a 0.38 M iron II solution.

In order to calculate the activity, a phosphate calibration curve was produced with a $KH_2PO_4$ range of 0 to 10 µmol/mL. By using the reaction conditions described above, the phytase activity of the test samples was calculated by applying the following formula: phytase activity in U/mL=[(OD 620 nm)×(dilution factor)]/[(slope of calibration curve)×(reaction time in minutes)].

The protein concentrations were calculated using the conventional Bradford method familiar to the skilled person.

FIG. 7 shows that the relative activities as a function of time (0 to 15 minutes) were higher for the mutants PHY-98-4X and PHY-98-6X compared with the enzyme of origin PHY-98 in *Saccharomyces cerevisiae*.

Example 5

Characterization of Thermostability of Enhanced Phytase Variants of *Yersinia intermedia*

The thermostability of variants isolated from the phytase of *Yersinia intermedia* was determined by measuring a residual activity of various supernatants from production of the variants either after pre-heating to a constant temperature for varying times or after a fixed pre-heating time at varying temperatures. In the first alternative, the variants were pre-heated to 80° C. for times of 0 to 30 minutes. In the second alternative, two types of residual variant activity were measured either after pre-heating for 15 minutes to temperatures of 45° C. to 65° C., or after pre-heating for 1 minute to temperatures of 60° C. to 80° C. The residual activities were determined in the first alternative as the % activity of the same sample without pre-heating or in the second alternative as the % of the activity of the same sample pre-heated to the first measured temperature, the two reference activities being considered as the 100% points. The residual activity is shown as raw values for the optical density at 600 nm after pre-heating for 15 minutes in FIG. 4.

FIGS. 3, 4 and 5 show the results obtained for the variants PHY-98-4X and PHY-98-6X expressed by *Saccharomyces cerevisiae* compared with the enzyme of origin PHY-98. FIG. 3 shows the higher residual activities of the two mutants PHY-98-4X and PHY-98-6X after pre-heating for 0 to 2 minutes at 80° C. compared with the enzyme of origin PHY-98. FIG. 4 shows the high residual activities of the two mutants PHY-98-4X and PHY-98-6X after pre-heating for 15 minutes at temperatures varying from 45° C. to 65° C. FIG. 5 shows the high residual activities of the two mutants PHY-98-4X and PHY-98-6X beyond 60° C. using 1 minute of pre-heating.

FIGS. 6a) and 6b) show the high residual activities of the mutants PHY-98-6X and PHY-98-6X-SS11, expressed by *Pichia pastoris*, after pre-heating times at 80° C. of respectively 0 to 30 minutes and 0 to 5 minutes.

Example 6

Thermostability of Mutants in Granulation Tests

Granulation tests could be carried out to determine the thermostability of the various mutants relative to the wild type and existing and/or commercially available enzymes. The various phytases could be incorporated into methods of forming and formulating granules intended to be added to animal feed, for example.

These granules could be formed by mixing/kneading supernatants from the production of the mutants and reference enzymes that have to be compared, for example a matrix composed of corn starch and water, under the same conditions. The granulation matrix may contain different relative phytase/corn/water percentages. Conventionally, after kneading, the matrix can be extruded with an extruder similar to the NICA™ E-220 type and spheronized directly using a NICA™ or Fuji Paudal™ QJ-400G type spheronizer. The particles obtained are then dried in a Glatt GPCG 1.1 type fluidized bed drier. The phytase activity in the granules is generally in the range 2500 to 3000 FTU/g.

The granules formed may be mixed with food. Depending on the volume of the tests, the quantity of food formed may vary. As an example, 250 g of granules may be mixed with 25 kg of food to form a pre-mix. Just before the test, this pre-mix may be incorporated into 225 kg of food, for example, with the same composition. In non-limiting manner, a typical poultry feed may be composed of 45% to 50% corn, 0 to 5% peas, 0 to 4.5% rape flour, 0 to 4.5% sunflower seed flour, 0 to 2.5% corn flour gluten, 6% to 10% whole soya beans, approximately 25% soya meal, approximately 4% tapioca, 1% to 3.5% of soya oil, 0 to 4% of animal fat, 0.5% to 1% of a cocktail of vitamins (Mervit 100), approximately 1% of powdered chalk, 0.2% to 1.3% of monocalcium phosphate, 0.1% to 0.4% of salts, 0 to 0.3% of sodium bicarbonate ($NaHCO_3$), 0.05% to 0.3% of L-lysine, 0.15% to 0.25% of DL-methionine and 0 to 0.05% of L-threonine. A pre-mix of approximately 25 kg can typically be mixed in a Collete MP90 type planetary mixer for 10 minutes. A mixture of the order of 225 kg can be mixed in a Nauta type 1200 liter mixer. Samples of this mixture are taken at this stage to determine the activity and stability of the mutants and the reference phytases before forming the final granules. A mixture of the order of 250 kg is typically dosed into the mixer/conditioner using a dosing screw at a rate of approximately 600 kg/hour where it is heated by injecting steam at approximately 95° C. The total residence time is approximately 10 to 30 seconds, after which the hot mixture is directed towards a granulating press. For the tests, the sizes of the granules that could be produced were of the type 5/45 mm (width/length) or 3/65 mm. The temperature of the granules at the outlet from the press is typically 82° C. to 83° C. for the first type of granules and 91° C. to 93° C. for the second type. Following this step, the granules are cooled on a cooling mat from which samples are taken in order to determine the activity and stability of the mutants and reference phytases after formation of the final granules. Granulation yields in terms of activity may thus be obtained for each mutant, compared with the reference enzymes, by producing activity reports after and before the granulation step. A protocol for measuring phytase activity is given in Example 4. In addition, a standard protocol for measuring phytase activity adapted to these methods has been published with the following reference: van. Engelen et al., Journal of AOAC International 1994, 77:760-764.

Example 7

Tests in Animal Feed Trials

Several approaches could be used to measure the effectiveness of the mutants of the invention in liberating phosphate from phytate in vivo in order to contribute to animal growth compared with reference phytases.

Various animals such as pigs could be integrated into well-established protocols. These had free access to water and a typical diet constituted, for example, by 67% corn, 28% soya flour, 1% powdered chalk, 0.1% L-lysine, 1% corn oil, 0.25% of a conventional vitamin cocktail, 0.5% salts, 0.5% antibiotics. The feed waste was collected daily. The weight gain of the animals was measured weekly to calculate the mean gain per day, the mean daily food intake and the gain/intake ratio. The mutants with a particular advantage and the best performances were typically those which had an increased gain/intake ratio.

In addition, in vitro models exist that can simulate digestion in the tract of a monogastric animal. As an example, feed samples composed of 30% soya flour and 70% corn flour may be supplemented with calcium phosphate in an amount of 5 g/kg of feed and preincubated at 40° C., pH 3 for 30 minutes, followed by adding pepsin in an amount of 3000 U/g of feed and various dosages of phytase in the range 0 (blank control) to 1 U of phytase/g of feed. Various phytase mutants could be tested and compared with reference phytases. The various samples were incubated at 40° C., initially at a pH of 3 for 60 minutes then at a pH of 4 for 30 minutes. The reactions were then stopped and the phytate and inositol phosphates were extracted by adding hydrochloric acid in a final concentration of 0.5M, incubating for 2 hours at 40° C., followed by a freeze-thaw cycle and one hour's incubation at 40° C.

The phytate and the inositol phosphates were separated by high performance ion exchange chromatography as described by Q. C. Chen, and B. W. Li (2003), Journal of Chromatography A 1018, 41-52 as well as by E. Skoglund, N. G. Carlson, and A. S. Sandberg (1997), J. Agric. Food Chem. 45, 431-436. The phosphate that was liberated was calculated from the difference between the phosphate bound to the inositol phosphates in the samples treated with phytase compared with the samples not treated with a phytase. The mutants of interest released a larger quantity of phosphate.

Biological Material Deposits:

Three bacterial strains containing the constructs PHY-98, PHY-98-6X and PHY-98-6X-SS11 used in the above examples were deposited with the Collection Nationale de Cultures de Microorganismes (CNCM) at the Institut Pasteur, 25, Rue du Docteur Roux, 75724 Paris Cedex France, under the terms of the Treaty of Budapest:

| Identifying references of deposited strains | Deposit date | Accession numbers for biological material received |
| --- | --- | --- |
| PHY-98 | Jun. 24, 2009 | CNCM I-4172 |
| PHY-98-6X | Jun. 24, 2009 | CNCM I-4173 |
| PHY-98-6X-SS11 | Jun. 24, 2009 | CNCM I-4174 |

LITERATURE CITED

D. J. Cosgrove (1970) inositol phosphate phosphatases of microbiological origin, inositol phosphate intermediates in the dephosphorylation of the hexaphosphates of myo-inositol, scyllo-inositol, and D-chiro-inositol by a bacterial (*Pseudomonas* sp.) phytase. Australian journal of Biological Sciences 23:1207-1220

Cullen et al. (1987) Sequence and centromere proximal location of a transformation enhancing fragment ans1 from *Aspergillus nidulans*. Nucleic Acids Research 15: 9163-75

J. Dassa et al. (1990) The complete nucleotide sequence of the *Escherichia coli* gene appA reveals significant homology between pH 2.5 acid phosphatase and glucose-1-phosphatase. J. Bacteriol. 172:5497-5500

Gems et al. (1991) An autonomously replicating plasmid transforms *Aspergillus nidulans* at high frequency. Gene 98:61-67

Greiner et al, Purification and characterization of two phytases from *E. Coli*. Arch. Biochem. Biophys., 303, 107-113, 1993

J. C. Janson and L. Ryden (1989) Protein Purification, VCH Publishers, New York

T. Karhunen, A. Mäntylä, K. M. H. Nevalainen, P. L. Suominen (1993) High frequency one-step gene replacement in *Trichoderma reesei*. I. Endoglucanase I overproduction. Mol Gen Genet 241: 515-522

U. K. Laemmli (1970) Cleavage of structural protein during the assembly of the head of bacteriophage T4. Nature 227: 680-685

Lim et al., 2000, Crystal structures of *Escherichia coli* phytase and its complex with phytate. Nat. Struct. Biol. 7: 108-113

Needleman and Wunsch (1970) A general method applicable to the search for similarities in the amino acid sequence of two proteins. J. Mol. Biol. 48: 443

Oshima et al. (1996) A 718-kb DNA sequence of the *Escherichia coli* K-12 genome corresponding to the 12.7-28.0 min region on the linkage map. DNA Research, 3:137-155

Pearson and Lipman (1988) Enhanced tools for biological sequence comparison. Proc. Natl. Acad. Sci. USA 85 (8): 2444-8

M. Penttilä, H. Nevalainen, M. Rättö, E. Salminen, J. Knowles (1987) A versatile transformation system for the cellulolytic filamentous fungus *Trichoderma reesei*. Gene 61: 155-164

V. K. Powar and V. Jagannathan (1982) Purification and properties of phytate-specific phosphatase from *Bacillus subtilis*. Journal of Bacteriology 151:1102-1108

U. Raeder, P. Broda (1985) Rapid preparation of DNA from filamentous fungi. Lett Appl Microbiol 1: 17-20

T. J. Richmond (1984) Solvent accessible surface area and excluded volume in proteins. J. Mol. Biol., 178, 63-89

Rodriguez et al. (2000) Site-directed mutagenesis improves catalytic efficiency and thermostability of *Escherichia coli* pH 2.5 acid phosphatase/phytase expressed in *Pichia pastoris*. Arch. Biochem. Biophys., 382:105-112

Saboulard et al (2005) High-throughput site-directed mutagenesis using oligonucleotides synthesized on DNA chips. Biotechniques September 39(3): 363-8

Smith and Waterman (1981) Ad. App. Math. 2: 482

Touati and Danchin (1987) The structure of the promoter and amino terminal region of the pH 2.5 acid phosphatase structural gene (appA) of *E. coli*: a negative control of transcription mediated by cyclic AMP. Biochimie, 69:215-221

Wyss et al (1999) Biochemical Characterization of Fungal Phytases. Appl Environ Microbiol 65 (2) 367-373

TABLE 1

| | | | | | |
|---|---|---|---|---|---|
| P3L | P3V | V4G | A5P | P8N | P8V |
| T9I | T9Q | T9S | T9Y | G10A | G10P |
| V16M | V17W | L19G | S20C | R21F | H22A |
| H22S | H22Y | G23S | R25C | P27F | T28N |
| T28S | T28V | Q30R | Q32R | L33R | T41G |
| G50D | G50E | V60I | Y67F | Y67W | G75R |
| A78P | D92R | D94G | D94S | Q95V | R96A |
| T97N | V125N | D126Q | H130N | H130Q | H130R |
| H130W | P131S | V132W | D133G | D133P | D133R |
| D133V | D133W | D140E | D140F | L152N | L152P |
| L156N | F167N | C182N | F197V | K206A | T209C |
| K210C | K210E | K210S | K210T | K210V | K210Y |
| V211C | V211G | L217N | L223S | E225D | F227S |
| L229H | Q230T | N231K | A234K | P236N | S251N |
| L252M | H256A | H256E | H256P | N257I | Q259K |
| Q259Y | D261F | A264P | Y268N | Y268E | K273N |
| G274S | P276L | Q292P | P297S | Q301L | H310R |
| D311A | D311E | D311G | T312D | T312N | T312P |
| T312V | N313F | N313R | I314E | I314M | A323E |
| P331R | D332A | D332L | D332Q | N333V | P335C |
| P335G | P335R | P335S | V341A | V341E | E343A |
| E343G | D349N | R353C | Y354N | V355W | A370D |
| A370T | K376S | P379L | G381S | S393G | P414Q |

TABLE 2

| <35% ASA | <35% ASA | <35% ASA | 35% < x <70% ASA | >70% ASA |
|---|---|---|---|---|
| Q7N | S220N | P335S | Y51N | K29N |
| D36N | Q230N | P335T | C81N | T142N |
| P39N | Q233S | Q352S | Q95N | A177N |
| R98N | Q233T | Q352T | D140N | A177S |
| Q143N + H145T | R242N | E371S | P155N | A177T |
| E158N | Q259S | E371T | G189N | K201N |
| E158N + S160T | Q259T | P379S | K210N | G293N |
| P207N | A264N | P379T | I250S | Q326S |
| P207S | K273N | A380S | I250T | Q326T |
| P207T | P300N | A380T | P297N | E391N |
| S212N | H310N | G394S | D349S | |
| A218N | D332N | G394T | D349T | |

TABLE 3

SER20-GLY339
VAL24-GLY56
SER26-TRP45
GLN30-MET34
LEU52-LEU99
THR53-GLY56
ALA57-ALA103
GLY101-VAL116
ALA147-TYR268
ASP193-ASN196
GLY274-ASN316
GLY322-ASP388

TABLE 4

Table 4A

| Mutants | K210S | Y268E | Q292P |
|---|---|---|---|
| 80%-20% activity extinction coefficients | 1.75 | 1.98 | 2.3 |

Table 4B

| | Wild type | K210S |
|---|---|---|
| T, °C. 80% | 50.77 | 50.51 |
| T, °C. 20% | 53.44 | 55.17 |
| Delta. 80%-20% | 2.67 | 4.66 |
| R (K210S/WT) | | 1.74531835 |

Table 4C

| Mutants | T142N | A177T | Q326T |
|---|---|---|---|
| 80%-20% activity extinction coefficients | 1.62 | 1.62 | 1.52 |

Table 4D

| Mutants | G274C/N316C(SS11) |
|---|---|
| 80%-20% activity extinction coefficients | 2.33 |

TABLE 5

Table 5A

| | | | | |
|---|---|---|---|---|
| L19 | S20 | R21 | H22 | G23 | V24 |
| R25 | S26 | P27 | T28 | K29 | Q30 |
| T31 | M34 | A49 | G50 | Y51 | L52 |
| D92 | V93 | D94 | Q95 | R96 | T97 |
| R98 | T100 | V125 | D126 | F129 | H130 |
| D133 | P207 | T209 | K210 | V211 | S212 |
| L213 | L217, | A218, | L219, | S220, | S221, |
| T222 | L223 | G224 | E225 | I226 | F227 |
| L228 | L229 | L253 | L255 | H256 | N257 |
| Q259 | F260 | M263 | A264 | K273 | L277 |
| G308 | G309 | H310 | D311 | T312 | N313 |
| I314 | A315 | N316 | D332 | N333 | T334 |
| P335 | P336 | G337 | G338 | | |

Table 5B

| | | | | | |
|---|---|---|---|---|---|
| Q30D | Y51G | Y51Q | Y51W | L52G | V93G |
| R98T | F129W | H130Y | P155T | L219V | L255T |
| M263L | G308S | | | | |

The invention claimed is:

1. An isolated enhanced phytase variant that comprises an amino acid sequence which is identical to SEQ ID NO: 2 except for six substitutions corresponding to substitutions T142N, A177T, K210S, Y268E, Q292P and Q326T in SEQ ID NO: 2.

2. An isolated enhanced phytase variant that comprises an amino acid sequence which is identical to SEQ ID NO: 2 except for eight substitutions corresponding to substitutions T142N, A177T, K210S, Y268E, Q292P, Q326T, G274C and N316C in SEQ ID NO: 2.

3. An isolated enhanced phytase variant that comprises an amino acid sequence which is identical to SEQ ID NO: 2 except for eight substitutions corresponding to substitutions T142N, A177T, K210S, Y268E, Q292P, Q326T, L52C and L99C in SEQ ID NO: 2.

4. A composition comprising the isolated enhanced phytase variant according to claim 1.

5. A composition comprising the isolated enhanced phytase variant according to claim 2.

6. A composition comprising the isolated enhanced phytase variant according to claim 3.

7. An animal feed comprising the isolated enhanced phytase variant according to claim 1.

8. An animal feed comprising the isolated enhanced phytase variant according to claim 2.

9. An animal feed comprising the isolated enhanced phytase variant according to claim 3.

10. An isolated enhanced phytase variant expressed by a host cell modified to introduce in said host cell a nucleic acid encoding said variant, wherein said variant comprises an amino acid sequence identical to SEQ ID NO: 2 except for six substitutions corresponding to substitutions T142N, A177T, K210S, Y268E, Q292P and Q326T in SEQ ID NO: 2.

11. An isolated enhanced phytase variant expressed by a host cell modified to introduce in said host cell a nucleic acid encoding said variant, wherein said variant comprises an amino acid sequence identical to SEQ ID NO: 2 except for eight substitutions corresponding to substitutions T142N, A177T, K210S, Y268E, Q292P, Q326T, G274C and N316C in SEQ ID NO: 2.

12. An isolated enhanced phytase variant expressed by a host cell modified to introduce in said host cell a nucleic acid encoding said variant, wherein said variant comprises an amino acid sequence identical to SEQ ID NO: 2 except for eight substitutions corresponding to substitutions T142N, A177T, K210S, Y268E, Q292P, Q326T, L52C and L99C in SEQ ID NO: 2.

13. A composition comprising the isolated enhanced phytase variant according to claim 10.

14. A composition comprising the isolated enhanced phytase variant according to claim 11.

15. A composition comprising the isolated enhanced phytase variant according to claim 12.

16. An animal feed comprising the isolated enhanced phytase variant according to claim 10.

17. An animal feed comprising the isolated enhanced phytase variant according to claim 11.

18. An animal feed comprising the isolated enhanced phytase variant according to claim 12.

* * * * *

```
                        SEQUENCE LISTING

<160> NUMBER OF SEQ ID NOS: 2

<210> SEQ ID NO 1
<211> LENGTH: 1257
<212> TYPE: DNA
<213> ORGANISM: Yersinia intermedia
<220> FEATURE:
<221> NAME/KEY: CDS
<222> LOCATION: (1)..(1257)

<400> SEQUENCE: 1 gca gcg ccg gtt gcg att cag ccg acc ggc tat acc ctg gaa cgt gtg      48
Ala Ala Pro Val Ala Ile Gln Pro Thr Gly Tyr Thr Leu Glu Arg Val
1               5                  10                  15 gtg att ctg agc cgt cat ggc gtt cgt agc ccg acc aaa cag acc cag      96
Val Ile Leu Ser Arg His Gly Val Arg Ser Pro Thr Lys Gln Thr Gln
            20                  25                  30 ctg atg aac gat gtg acc ccg gat aaa tgg ccg cag tgg ccg gtt gcg     144
Leu Met Asn Asp Val Thr Pro Asp Lys Trp Pro Gln Trp Pro Val Ala
        35                  40                  45 gcg ggt tat ctg acc ccg cgt ggc gcg cag ctg gtt acc ctg atg ggc     192
Ala Gly Tyr Leu Thr Pro Arg Gly Ala Gln Leu Val Thr Leu Met Gly
    50                  55                  60 ggc ttt tat ggc gat tat tat cgt agc cag ggc ctg ctg gca gcg ggt     240
Gly Phe Tyr Gly Asp Tyr Tyr Arg Ser Gln Gly Leu Leu Ala Ala Gly
65                  70                  75                  80 tgt ccg acc gat gcg gtg att tat gcg cag gcg gat gtg gat cag cgt     288
Cys Pro Thr Asp Ala Val Ile Tyr Ala Gln Ala Asp Val Asp Gln Arg
                85                  90                  95 acc cgt ctg acc ggc cag gcg ttt ctg gat ggc atc gcg ccg ggt tgt     336
Thr Arg Leu Thr Gly Gln Ala Phe Leu Asp Gly Ile Ala Pro Gly Cys
            100                 105                 110 ggc ctg aaa gtg cat tat cag gcg gat ctg aaa aaa gtg gat ccg ctg     384
Gly Leu Lys Val His Tyr Gln Ala Asp Leu Lys Lys Val Asp Pro Leu
        115                 120                 125 ttt cat ccg gtg gat gcg ggc gtg tgc aaa ctg gat agc acc cag acc     432
```

```
              Phe His Pro Val Asp Ala Gly Val Cys Lys Leu Asp Ser Thr Gln Thr
                  130                 135                 140 cat aaa gcg gtg gaa gaa cgt ctg ggc gct ccg ctg tct gaa ctg agc         480
His Lys Ala Val Glu Glu Arg Leu Gly Ala Pro Leu Ser Glu Leu Ser
145                 150                 155                 160 aaa cgt tat gcg aaa ccg ttt gcg cag atg ggc gaa att ctg aac ttt         528
Lys Arg Tyr Ala Lys Pro Phe Ala Gln Met Gly Glu Ile Leu Asn Phe
                165                 170                 175 gcg gcg agc ccg tat tgc aaa agc ctg cag cag cag ggc aaa gtg tgc         576
Ala Ala Ser Pro Tyr Cys Lys Ser Leu Gln Gln Gln Gly Lys Val Cys
            180                 185                 190 gat ttt gcg aat ttt gtg gcg aac aaa atc acc gtg aac aaa ccg ggc         624
Asp Phe Ala Asn Phe Val Ala Asn Lys Ile Thr Val Asn Lys Pro Gly
        195                 200                 205 acc aaa gtg agc ctg agc ggt ccg ctg gcc ctg agc agc acc ctg ggc         672
Thr Lys Val Ser Leu Ser Gly Pro Leu Ala Leu Ser Ser Thr Leu Gly
    210                 215                 220 gaa att ttt ctg ctg cag aac agc caa gcg atg ccg gat gtg gcg tgg         720
Glu Ile Phe Leu Leu Gln Asn Ser Gln Ala Met Pro Asp Val Ala Trp
225                 230                 235                 240 cat cgc ctg acc ggc gaa gat aac tgg att agc ctg ctg tct ctg cat         768
His Arg Leu Thr Gly Glu Asp Asn Trp Ile Ser Leu Leu Ser Leu His
                245                 250                 255 aac gcg cag ttt gat ctg atg gcg aaa acc ccg tat att gcg cgt cat         816
Asn Ala Gln Phe Asp Leu Met Ala Lys Thr Pro Tyr Ile Ala Arg His
            260                 265                 270 aaa ggc acc ccg ctg ctg caa caa att gaa acc gcg ctg gtg ctg cag         864
Lys Gly Thr Pro Leu Leu Gln Gln Ile Glu Thr Ala Leu Val Leu Gln
        275                 280                 285 cgt gat gcg cag ggt cag acg ctg ccg ctg tct ccg cag acg aaa att         912
Arg Asp Ala Gln Gly Gln Thr Leu Pro Leu Ser Pro Gln Thr Lys Ile
    290                 295                 300 ctg ttt ctg ggc ggc cat gat acc aac att gcg aat att gcg ggc atg         960
Leu Phe Leu Gly Gly His Asp Thr Asn Ile Ala Asn Ile Ala Gly Met
305                 310                 315                 320 ctg ggc gcg aat tgg caa ctg ccg cag cag ccg gat aat act ccg ccg        1008
Leu Gly Ala Asn Trp Gln Leu Pro Gln Gln Pro Asp Asn Thr Pro Pro
                325                 330                 335 ggc ggt ggt ctg gtg ttt gaa ctg tgg cag aat ccg gat aac cat cag        1056
Gly Gly Gly Leu Val Phe Glu Leu Trp Gln Asn Pro Asp Asn His Gln
            340                 345                 350 cgt tat att gcg gtg aaa atg ttt tat cag acc atg ggc cag ctg cgt        1104
Arg Tyr Ile Ala Val Lys Met Phe Tyr Gln Thr Met Gly Gln Leu Arg
        355                 360                 365 aac gcg gaa aaa ctg gac ctg aaa aac aat ccg gcg ggt cgt gtg ccg        1152
Asn Ala Glu Lys Leu Asp Leu Lys Asn Asn Pro Ala Gly Arg Val Pro
    370                 375                 380 gtg gcg att gat ggc tgc gaa aac agc ggc gat gat aaa ctg tgc cag        1200
Val Ala Ile Asp Gly Cys Glu Asn Ser Gly Asp Asp Lys Leu Cys Gln
385                 390                 395                 400 ctg gat acc ttt cag aaa aaa gtg gcg cag gcg att gaa ccg gcg tgc        1248
Leu Asp Thr Phe Gln Lys Lys Val Ala Gln Ala Ile Glu Pro Ala Cys
                405                 410                 415 cat att taa                                                            1257
His Ile <210> SEQ ID NO 2
<211> LENGTH: 418
<212> TYPE: PRT
<213> ORGANISM: Yersinia intermedia
```

<400> SEQUENCE: 2

```
Ala Ala Pro Val Ala Ile Gln Pro Thr Gly Tyr Thr Leu Glu Arg Val
1               5                   10                  15

Val Ile Leu Ser Arg His Gly Val Arg Ser Pro Thr Lys Gln Thr Gln
                20                  25                  30

Leu Met Asn Asp Val Thr Pro Asp Lys Trp Pro Gln Trp Pro Val Ala
            35                  40                  45

Ala Gly Tyr Leu Thr Pro Arg Gly Ala Gln Leu Val Thr Leu Met Gly
        50                  55                  60

Gly Phe Tyr Gly Asp Tyr Arg Ser Gln Gly Leu Leu Ala Ala Gly
65                  70                  75                  80

Cys Pro Thr Asp Ala Val Ile Tyr Ala Gln Ala Asp Val Asp Gln Arg
                85                  90                  95

Thr Arg Leu Thr Gly Gln Ala Phe Leu Asp Gly Ile Ala Pro Gly Cys
                100                 105                 110

Gly Leu Lys Val His Tyr Gln Ala Asp Leu Lys Lys Val Asp Pro Leu
            115                 120                 125

Phe His Pro Val Asp Ala Gly Val Cys Lys Leu Asp Ser Thr Gln Thr
            130                 135                 140

His Lys Ala Val Glu Glu Arg Leu Gly Ala Pro Leu Ser Glu Leu Ser
145                 150                 155                 160

Lys Arg Tyr Ala Lys Pro Phe Ala Gln Met Gly Glu Ile Leu Asn Phe
                165                 170                 175

Ala Ala Ser Pro Tyr Cys Lys Ser Leu Gln Gln Gln Gly Lys Val Cys
            180                 185                 190

Asp Phe Ala Asn Phe Val Ala Asn Lys Ile Thr Val Asn Lys Pro Gly
            195                 200                 205

Thr Lys Val Ser Leu Ser Gly Pro Leu Ala Leu Ser Ser Thr Leu Gly
        210                 215                 220

Glu Ile Phe Leu Leu Gln Asn Ser Gln Ala Met Pro Asp Val Ala Trp
225                 230                 235                 240

His Arg Leu Thr Gly Glu Asp Asn Trp Ile Ser Leu Ser Leu His
                245                 250                 255

Asn Ala Gln Phe Asp Leu Met Ala Lys Thr Pro Tyr Ile Ala Arg His
            260                 265                 270

Lys Gly Thr Pro Leu Leu Gln Gln Ile Glu Thr Ala Leu Val Leu Gln
        275                 280                 285

Arg Asp Ala Gln Gly Gln Thr Leu Pro Leu Ser Pro Gln Thr Lys Ile
290                 295                 300

Leu Phe Leu Gly Gly His Asp Thr Asn Ile Ala Asn Ile Ala Gly Met
305                 310                 315                 320

Leu Gly Ala Asn Trp Gln Leu Pro Gln Gln Pro Asp Asn Thr Pro Pro
            325                 330                 335

Gly Gly Gly Leu Val Phe Glu Leu Trp Gln Asn Pro Asn His Gln
            340                 345                 350

Arg Tyr Ile Ala Val Lys Met Phe Tyr Gln Thr Met Gly Gln Leu Arg
            355                 360                 365

Asn Ala Glu Lys Leu Asp Leu Lys Asn Asn Pro Ala Gly Arg Val Pro
370                 375                 380
```

```
Val Ala Ile Asp Gly Cys Glu Asn Ser Gly Asp Asp Lys Leu Cys Gln
385             390             395             400

Leu Asp Thr Phe Gln Lys Lys Val Ala Gln Ala Ile Glu Pro Ala Cys
                405             410             415

His Ile
```